(12) United States Patent
Sagawa et al.

(10) Patent No.: US 7,816,134 B2
(45) Date of Patent: Oct. 19, 2010

(54) METHOD OF EXTENSIVE CULTURE OF ANTIGEN-SPECIFIC CYTOTOXIC T CELLS

(75) Inventors: Hiroaki Sagawa, Kusatsu (JP); Mitsuko Ideno, Kyoto (JP); Ikunoshin Kato, Uji (JP)

(73) Assignee: Takara Bio Inc., Shiga (JP)

( * ) Notice: Subject to any disclaimer, the term of this patent is extended or adjusted under 35 U.S.C. 154(b) by 1340 days.

(21) Appl. No.: 10/344,534

(22) PCT Filed: Aug. 15, 2001

(86) PCT No.: PCT/JP01/07032

§ 371 (c)(1),
(2), (4) Date: Feb. 12, 2003

(87) PCT Pub. No.: WO02/14481

PCT Pub. Date: Feb. 21, 2002

(65) Prior Publication Data

US 2004/0115809 A1    Jun. 17, 2004

(30) Foreign Application Priority Data

Aug. 16, 2000    (JP) ............................. 2000-247072

(51) Int. Cl.
*C12N 5/08* (2006.01)
*C12N 5/00* (2006.01)
*C12N 5/02* (2006.01)

(52) U.S. Cl. .................... 435/372; 435/372.3; 435/375; 435/377

(58) Field of Classification Search ................ 435/372, 435/372.3, 386, 383
See application file for complete search history.

(56) References Cited

U.S. PATENT DOCUMENTS 5,827,642 A * 10/1998 Riddell et al. .................. 435/2
6,316,257 B1 * 11/2001 Flyer et al. ............... 435/372.3
6,734,014 B1 * 5/2004 Hwu et al. .................. 435/325

2005/0042208 A1 * 2/2005 Sagawa et al. ............. 424/93.7

FOREIGN PATENT DOCUMENTS

| WO | WO 96/06929 A2 | 3/1996 |
|---|---|---|
| WO | WO 97/32970 A1 | 9/1997 |
| WO | WO-98/12306 A1 | 3/1998 |
| WO | WO-98/33888 A1 | 8/1998 |

OTHER PUBLICATIONS

Riddell et al Science 1992, V.257 pp. 238-241.*
Galandrini et al., J. of Immunology, 1994,v.153, pp. 21-31.*
Stanley R. Riddell et al.; Science, vol. 257, pp. 238-241, 1992.
Ikunoshin Kato et al.; Jpn. J. Phycol.; Mar. 2000, vol. 48, pp. 13-19.
Kohei Noguchi et al.; Anticancer Research, 1995, vol. 15, pp. 255-288.
Stanley R. Riddell; The Journal of Immunology, vol. 146, No. 8, pp. 2795-2804, Apr. 15, 1991.
Stanley R. Riddell et al.; Journal of Immunological Methods, vol. 128, pp. 189-201, 1990.
Maria A. Bednarek et al.; The Journal of Immunology, vol. 147, No. 12, pp. 4047-4053, Dec. 15, 1991.
J. Carter et al.; Immunology 1986, vol. 57, pp. 123-129.
Joseph P. Uberti et al.; Clinical Immunology and Immunopathology; vol. 70, No. 3, Mar. 1994, pp. 234-240.
Riddell et al., Science, (1992), vol. 257, pp. 238-241.
Kato et al., Sourui, Mar. 2000, vol. 48, pp. 13-19.
Noguchi et al., Anticancer Research, (1995), vol. 15, pp. 255-288.
Shun et al., Chin. J. Mar. Drugs, 14(3):909-913, 1996.
Shun et al., Chin. J. Mar. Drugs, 14(3):9-13, 1995.

* cited by examiner

*Primary Examiner*—Michail A Belyavskyi
(74) *Attorney, Agent, or Firm*—Birch, Stewart, Kolasch & Birch, LLP

(57) ABSTRACT

The present invention provides methods for inducing, maintaining and expanding CTL (cytotoxic T cell) having an antigen-specific cytotoxic activity at a high level, which is useful in the adoptive immunotherapy, by using as an effective ingredient at least one compound selected from the group consisting of acidic polysaccharides, acidic oligosaccharides, acidic monosaccharides, and salts thereof. The above-mentioned compounds include fucoidans, heparins, alginic acid, chondroitin sulfate A, chondroitin sulfate B, pectic acid, hyaluronic acid, degradation products of fucoidans, sulfated glucose, sulfated fucose and salts thereof.

7 Claims, 1 Drawing Sheet

SEQUENCE LISTING

<160> NUMBER OF SEQ ID NOS: 4

<210> SEQ ID NO 1
<211> LENGTH: 10
<212> TYPE: PRT
<213> ORGANISM: Artificial sequence
<220> FEATURE:
<223> OTHER INFORMATION: Designed peptide based on nucleoprotein derived
      from influenza virus.

<400> SEQUENCE: 1

Arg Phe Tyr Ile Gln Met Cys Thr Glu Leu
                 5                  10

<210> SEQ ID NO 2
<211> LENGTH: 9
<212> TYPE: PRT
<213> ORGANISM: Artificial sequence
<220> FEATURE:
<223> OTHER INFORMATION: Designed peptide based on matrixprotein derived
      from influenza virus.

<400> SEQUENCE: 2

Gly Ile Leu Gly Phe Val Phe Thr Leu
                 5

<210> SEQ ID NO 3
<211> LENGTH: 9
<212> TYPE: PRT
<213> ORGANISM: Artificial sequence
<220> FEATURE:
<223> OTHER INFORMATION: Designed peptide based on HLA A2.1 binding
      peptide derived from melanoma antigen MAGE3.

<400> SEQUENCE: 3

Phe Leu Trp Gly Pro Arg Ala Leu Val
                 5

<210> SEQ ID NO 4
<211> LENGTH: 9
<212> TYPE: PRT
<213> ORGANISM: Artificial sequence
<220> FEATURE:
<223> OTHER INFORMATION: Designed peptide based on HLA A2.1 binding
      peptide derived from melanoma antigen MART1.

<400> SEQUENCE: 4

Ala Ala Gly Ile Gly Ile Leu Thr Val
                 5

METHOD OF EXTENSIVE CULTURE OF ANTIGEN-SPECIFIC CYTOTOXIC T CELLS

This application is the national phase under 35 U.S.C. §371 of PCT International Application No. PCT/JP01/07032 which has an International filing date of Aug. 15, 2001, which designated the United States of America.

TECHNICAL FIELD

The present invention relates to methods for inducing, maintaining and expanding cytotoxic T cell having an antigen-specific cytotoxic activity, which is useful in the medical field.

BACKGROUND ART

A living body is protected from foreign substances mainly by an immune response, and an immune system has been established by various cells and the soluble factors produced thereby. Among them, leukocytes, especially lymphocytes, play a key role. The lymphocytes are classified in two major types, B lymphocyte (hereinafter referred to as B cell) and T lymphocyte (hereinafter referred to as T cell), both of which specifically recognize an antigen and act on the antigen to protect the living body.

T cell is subclassified to helper T cell having CD(Cluster Designation)4 marker (hereinafter referred to as $T_H$), mainly involved in assisting in antibody production and induction of various immune responses, and cytotoxic T cell having CD8 marker ($T_c$: cytotoxic T lymphocyte, also referred to as killer T cell, which may be hereinafter referred to as CTL), mainly exhibiting a cytotoxic activity. CTL, which plays the most important role in recognizing, destroying and eliminating tumor cell, virus-infected cell or the like, does not produce an antibody specifically reacting with an antigen like in B cell, but directly recognizes and acts on antigens (antigenic peptide) from a target cell which is associated with major histocompatibility complex (MHC, which may be also referred to as human leukocyte antigen (HLA) in human) Class I molecules present on the surface of the target cell membrane. At this time, T cell receptor (hereinafter referred to as TCR) existing on the surface of the CTL membrane specifically recognizes the above-mentioned antigenic peptides and MHC Class I molecules, and determines whether the antigenic peptide is derived from itself or nonself. Target cell which has been determined to be from nonself is then specifically destroyed and eliminated by CTL.

Recent years, a therapy which would cause a heavier physical burden on a patient, such as pharmacotherapy and radiotherapy, has been reconsidered, and an interest has increased in an immunotherapy with a lighter physical burden on a patient. Especially, there has been remarked an effectiveness of adoptive immunotherapy in which CTL capable of specifically reacting with an antigen of interest is induced in vitro from CTL or T cell derived from a human having normal immune function, and then transferred to a patient. For instance, it has been suggested that adoptive immunotherapy using an animal model is an effective therapy for virus infection and tumor (authored by Greenberg, P. D., *Advances in Immunology*, published in 1992). Further, use of CTL to a patient with congenital, acquired or iatrogenic T cell immunodeficiency has been remarked, from the fact that administration of CIL to a patient with immunodeficiency results in reconstruction of specific CIL response, by which cytomegalovirus is rapidly and persistently eliminated without showing toxicity [*Blood*, 78, 1373-1380 (1991)] and the like. In this therapy, it is important to maintain or increase the cell count with maintaining or enhancing the antigen-specific cytotoxic activity of the CTL. Also, as to maintenance and increase of the cell count of CTL, if an effective cell count in adoptive immunotherapy for human is deduced on the basis of the studies on an animal model, it is thought that $10^9$ to $10^{10}$ antigen-specific T cells are necessary (authored by Greenberg, P. D., Advances in Immunology, published in 1992). In other words, in adoptive immunotherapy, it can be said that it is a major problem to obtain the above cell count in vitro in a short period of time.

As to maintenance and enhancement of an antigen-specific cytotoxic activity of CTL, there has been generally employed a method of repeating stimulation with an antigen of interest when a specific response to an antigen for CTL is induced. However, in this method, the cell count may temporarily be increased, but the cell count is eventually decreased, and necessary cell count cannot be obtained. As its countermeasure, there are no other means in the current situation but to lyophilize the cells in an earlier stage during repeat of stimulation with an antigen, or to obtain antigen-specific CTL clones, lyophilize a part of the clones, and repeat antigen stimulation to the lyophilized cells after thawing if the cell count or antigen-specific cytotoxic activity of the CTL clones is lowered due to a long-term culture.

A method for establishing T cell by a long-term culture using mouse T cell has been reported [*Nature*, 294, 697-699 (1981)], which is a method for isolating T cell and establishing a cell strain therewith. However, it is impossible to proliferate T cell to $10^9$ to $10^{10}$ cells by this method. Next, U.S. Pat. No. 5,057,423 discloses a method comprising inducing lymphokine-activated killer (LAK) cell using a large amount of interleukin 2 (IL-2) in a high concentration, thereby increasing the cell count in 100 folds in 3 to 4 days. This cell count is enormous, considering that it usually takes about 24 hours for a single cell to be divided and proliferated into two cells. In addition, adoptive immunotherapy has been tried by inducing tumor-infiltrating lymphocyte (TIL) using IL-2 in a high concentration as above [*New Engl. J. Med.*, 316, 1310-1321 (1986); *New Engl. J. Med.*, 319, 1676-1680 (1988); *Blood*, 81, 2093-2101 (1993)]. However, the former is a method for obtaining T cell which is non-specific for an antigen, and in the latter, antigen specificity is very low, if any, because activated polyclonal lymphocyte population is used. Further, in both of the above-mentioned methods, IL-2 is used in a high concentration in order to promote cell proliferation. It is reported that apoptosis (cell death) may occur when T cell treated with IL-2 in a high concentration is stimulated with a specific antigen in the absence of IL-2 [*Nature*, 353, 858-861 (1991); *Eur. J. Immunol.*, 23, 1552-1560 (1992)]. Therefore, the effectiveness of LAK cell or TIL obtained by the above-mentioned methods is problematic.

In addition, when T cell is cultured at a low density ($5 \times 10^3$ to $1 \times 10^4$ cells/ml) in the presence of T-cell growth factor and IL-2, T cell rapidly proliferates over a period of 7 days, and eventually proliferates to a saturation density of 3 to $5 \times 10^5$ cells/ml. However, it is also reported that the cell always dies once the cell reaches the saturation density [*Immunological Rev.*, 54, 81-109 (1981)]. Therefore, LAK cell, TIL and the method for culturing T cell at a low density are problematic in both aspects of actual use and usefulness.

Next, regarding the antigen-specific CTL, there are reported adoptive immunotherapy in which allogenic cytomegalovirus(CMV)-specific CTL is cultured in vitro for 5 to 12 weeks to proliferate CTL, and then administered intravenously to a patient with immunodeficiency [Riddell et al., *Science*, 257:238-240, 1992]; and a method for isolating and expanding a CMV-specific CTL clone using self-CMV infected fibroblast and IL-2 [*J. Immunology,* 146, 2795-2804 (1991)] or using anti-CD3 monoclonal antibody (anti-CD3 mAb) and IL-2 [*J. Imm. Methods,* 128, 189-201 (1990)]. However, there is a serious problem in these methods. Specifically, it takes about 3 months to obtain $1 \times 10^9$ cells/ml of antigen-specific CTLS, during which time the symptoms of the patient advance, so that it is difficult to appropriately treat the disease depending on the situation.

As a method of solving the above-mentioned problem, WO 96/06929 discloses an REM method (rapid expansion method). This REM method is a method for expanding a primary T cell population containing antigen-specific CTL and $T_H$ in a short period of time. In other words, this method is characterized in that a large amount of T cell can be provided by expanding individual T cell clones. However, there is a problem as described below. In the REM method, antigen-specific CTL is expanded using anti-CD3 antibody, IL-2, and PBMC (peripheral blood monocyte) made deficient in an ability for proliferation by irradiation, and Epstein-Barr virus (EBV)-infected cells. However, there are problems that risk of admixing EBV-transformed B cell (EBV-B cell) into T cell is not deniable (problem in safety); that a large amount of PBMC (PBMC in an amount of about 40 times the number of antigen-specific CTL required) is required as feeder cell; that the antigen-specific cytotoxic activity of the expanded CTL cannot be sufficiently satisfactory; that the antigen-specific cytotoxic activity possessed by T cell is decreased with the cell proliferation when CTL is allowed to proliferate using a T cell population other than the T cell clone; and the like.

In other words, in a conventional method for preparing antigen-specific CTL, there have not been solved the problems essential to adoptive immunotherapy in which CTL having an antigen-specific cytotoxic activity effectively used in the treatment, is prepared in a sufficient amount for a short period of time.

An object of the present invention is to provide methods for inducing, maintaining and expanding CTL having an antigen-specific cytotoxic activity at a high level, which is suitably used in adoptive immunotherapy.

DISCLOSURE OF INVENTION

Concretely, the present invention relates to:
[1] a method for inducing cytotoxic T cell having an antigen-specific cytotoxic activity, characterized in that the method comprises the step of incubating a precursor cell capable of differentiating to cytotoxic T cell with an antigen presenting cell in the presence of at least one compound selected from the group consisting of acidic polysaccharides, acidic oligosaccharides, acidic monosaccharides, and salts thereof;
[2] the method according to item [1] above, wherein the compound is at least one compound selected from the group consisting of fucoidans, heparins, alginic acid, chondroitin sulfate A, chondroitin sulfate B, pectic acid, hyaluronic acid, degradation products of fucoidans, sulfated glucose, sulfated fucose and salts thereof;
[3] a method for maintaining cytotoxic T cell having an antigen-specific cytotoxic activity, characterized in that the method comprises the step of continuously culturing the cytotoxic T cell in the presence of at least one compound selected from the group consisting of acidic polysaccharides, acidic oligosaccharides, acidic monosaccharides, and salts thereof;
[4] the method according to item [3] above, wherein the compound is at least one compound selected from the group consisting of fucoidans, heparins, alginic acid, chondroitin sulfate A, chondroitin sulfate B, pectic acid, hyaluronic acid, degradation products of fucoidans, sulfated glucose, sulfated fucose and salts thereof;
[5] a method for expanding cytotoxic T cell having an antigen-specific cytotoxic activity, characterized in that the method comprises the step of incubating the cytotoxic T cell in the presence of at least one compound selected from the group consisting of acidic polysaccharides, acidic oligosaccharides, acidic monosaccharides and salts thereof;
[6] the method according to item [5] above, wherein the cytotoxic T cell is incubated further in the presence of anti-CD3 antibody in the above step;
[7] the method according to item [5] or [6] above, wherein the cytotoxic T cell is incubated together with a feeder cell in the above step;
[8] the method according to item [7] above, wherein the feeder cell is a non-virus-infected cell;
[9] the method according to any one of items [5] to [8] above, wherein the compound is at least one compound selected from the group consisting of fucoidans, heparins, alginic acid, chondroitin sulfate A, chondroitin sulfate B, pectic acid, hyaluronic acid, degradation products of fucoidans, sulfated glucose, sulfated fucose and salts thereof;
[10] a method for collecting cytotoxic T cell, comprising the step of selecting a cell population rich in cytotoxic T cell having an antigen-specific cytotoxic activity from a culture containing the cytotoxic T cell obtained by the method of any one of items [1] to [9] above;
[11] a cytotoxic T cell having an antigen-specific cytotoxic activity prepared by the method of any one of items [1] to [10] above; and
[12] a therapeutic agent, characterized in that the therapeutic agent comprises the cytotoxic T cell of item [11] above as an effective ingredient.

BEST MODE FOR CARRYING OUT THE INVENTION

Figure 1:
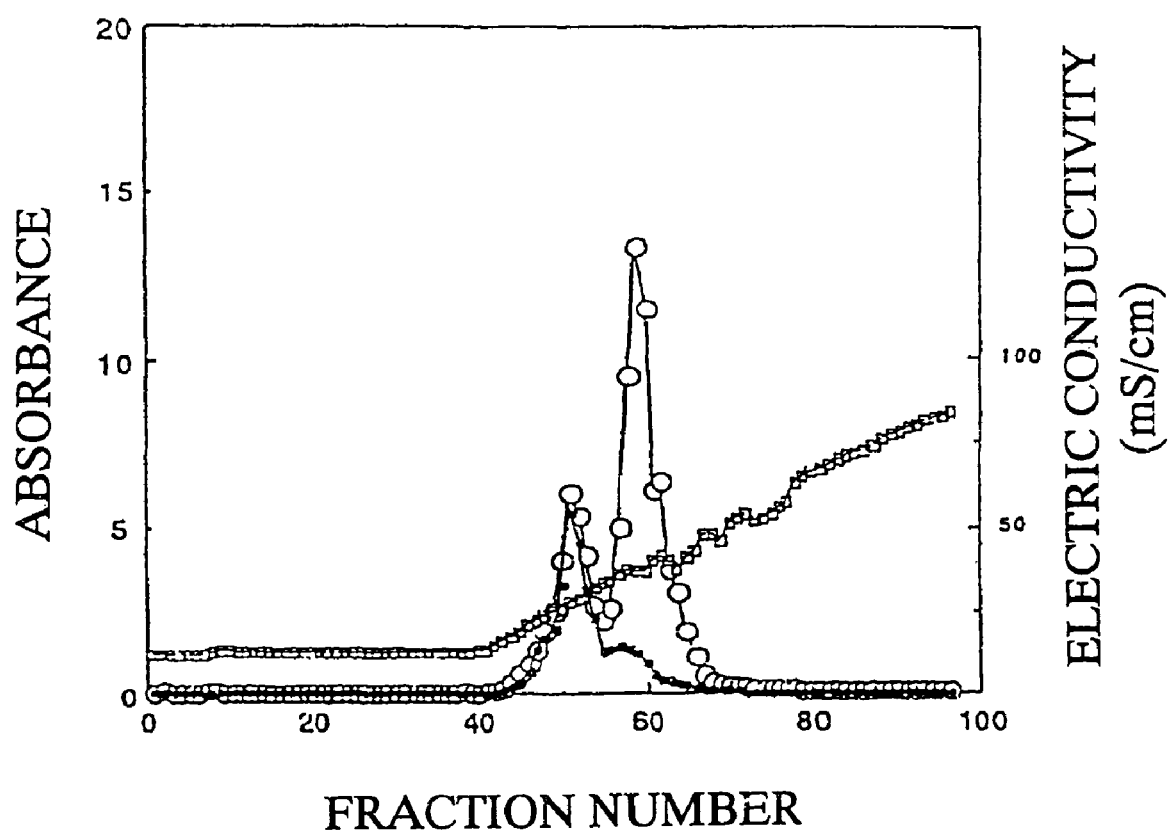
FIG. 1 is a graph showing an elution pattern of the fucoidan derived from *Kjellmaniella crassifolia* on DEAE-Cellulofine A-800 column.

In the present invention, it has been unexpectedly found that ability ("ability" may be also referred to herein as "action") for maintaining or enhancing an antigen-specific cytotoxic activity of CTL can be exhibited by at least one compound selected from the group consisting of acidic polysaccharides, acidic oligosaccharides, acidic monosaccharides, and salts thereof, and the present invention has been completed thereby. According to the present invention, there are provided methods for inducing, maintaining and expanding CTL having an antigen-specific cytotoxic activity at a high level, which are suitably used in adoptive immunotherapy, using the above-mentioned compound as an effective ingredient. Incidentally, in the case where the compound used as the effective ingredient of the present invention has D-form and L-form, both forms can be used, and use of the L-form is preferable.

The present invention will be concretely described below.

(1) Method for Inducing Cytotoxic T Cell of Present Invention

It has been known that CTL induced by antigen-presenting cell usually lowers its antigen-specific cytotoxic activity during the period of maintaining or proliferating CTL. According to the present invention, there is provided a method for inducing antigen-specific CTL by which the antigen-specific cytotoxic activity would not be markedly lowered as conventionally observed, even when the cell after induction is maintained or proliferated over a long period of time.

One of the great features of the method for inducing CTL of the present invention resides in that CTL is induced in the presence of the above-mentioned effective ingredient. CTL is induced by incubating a precursor cell capable of differentiating to CTL with an appropriate antigen-presenting cell in the presence of the effective ingredient in order to give the CTL obtained an ability of recognizing the desired antigen. The precursor cell is not particularly limited, as long as the precursor cell is a cell which is in a stage before the cell becomes CTL and fated to differentiate to CTL, and includes, for instance, peripheral blood monocyte (PBMC), naive T cell, memory T cell and the like. The antigen-presenting cell is not particularly limited, as long as the cell has an ability to present an antigen to be recognized to T cell. For instance, monocyte, B cell, T cell, macrophage, dendritic cell, fibroblast or the like which is allowed to present a desired antigen can be used in the present invention.

The antigen-presenting cell can be prepared by adding an antigenic peptide to a cell having an antigen-presenting ability, thereby allowing the cell to present the antigenic peptide on its surface (see, for instance, the publication: Bednarek M. A. et al., *J. Immunology* 147 p.4047-4053 (1991)). In addition, in the case where a cell having an antigen-presenting ability has an ability to process an antigen, the antigen is added to the cell, whereby the antigen is incorporated into the cell and processed therein, and fragmented antigenic peptides are presented on the cell surface. Incidentally, when an antigenic peptide is added to a cell having an antigen-presenting ability, an antigenic peptide matching the HLA restriction of the antigen-presenting cell used and the CTL to be induced are used.

Incidentally, the antigen used in the present invention is not particularly limited, and includes, for instance, exogenous antigens such as bacteria and viruses, endogenous antigens such as tumor-associated antigens (cancer antigens) and the like.

In the present invention, it is preferable that the antigen-presenting cell is made non-proliferative. In order to make the cell non-proliferative, for instance, the cell may be subjected to irradiation with X ray or the like, or a treatment with an agent such as mitomycin.

The medium used in the method for inducing CTL of present invention is not particularly limited. There can be used known media prepared by blending components necessary for maintenance or growth of CTL, a precursor cell thereof and an antigen-presenting cell. The media may be, for instance, commercially available ones. These media may contain appropriate proteins, cytokines, and other components in addition to the originally contained constituents. Preferably, a medium containing interleukin-2 (IL-2) is used in the present invention.

As the acidic polysaccharide used as the effective ingredient of the present invention, any of acidic polysaccharides derived from animal, derived from plant, derived from microorganism, and derived from marine algae, and synthetic acidic polysaccharides can be used. Also, phosphated polysaccharides, for instance, nucleic acids, are also encompassed by the acidic polysaccharide of the present invention.

As the acidic polysaccharide derived from animal, for instance, hyaluronic acid and various sulfated polysaccharides can be used, and chondroitin sulfate, keratan sulfate, dermatan sulfate, heparan sulfate, heparin and the like can be used as the sulfated polysaccharide. In addition, sulfated polysaccharides derived from Echinodermata such as sea cucumber, Echnoidea and Asterozoa, sulfated polysaccharides derived from Pisces such as cartilage of *Chondrichthyes Selachii* can be used in the present invention. Sulfated polysaccharides-containing sea cucumber includes, for instance, sea cucumber described in Japanese Patent Laid-Open No. Hei 4-91027, and sulfated polysaccharides can be prepared from sea cucumber by the method described in the publication.

As the acidic polysaccharide derived from plant, for instance, pectic acid or the like can be used.

As the acidic polysaccharide derived from microorganism, for instance, hyaluronic acid or xanthane can be used.

As the acidic polysaccharide derived from marine algae, for instance, acidic polysaccharides derived from Phaeophyceae, Rhodophyceae, Chlorophyceae or Cyanophyceae can be used.

As the acidic polysaccharide derived from Phaeophyceae, for instance, various sulfated polysaccharides can be used. For instance, fucoidan, sulfated fucogalactan, sulfated fucoglucuronomannan, glucuronoxylofucane, Sargassan, glucuronomannogalactan, xylofucoglucuronan, ascorfilan, glucuronogalactofucane, sulfated glucuronofucane and the like can be used.

In addition, Phaeophyceae used as a raw material include, for instance, Phaeophyceae belonging to Laminariales, Chordariales and Fucales, such as *Kjellmaniella crassifolia*, *Laminaria japonica*, Kjellmaniella, *Fucus vesiculosus*, Nemacystus, *Cladosiphon okamuranus*, Undaria, *Ecklonia kurome*, Eisenia, Ecklonia, *Lessonia nigrescence*, *Ascophyllum nodosum* and Giant kelp.

As the acidic polysaccharide derived from Phaeophyceae, a fucoidan is prepared from, for instance, *Kjellmaniella crassifolia*, and the resulting fucoidan can be separated into glucuronic acid-containing fucoidan (referred to as "U-fucoidan") and glucuronic acid non-containing fucoidan (referred to as "F-fucoidan"). Each of the fucoidans can be used as the effective ingredient of the present invention. Also, sulfated fucogalactan (hereinafter referred to as "G-fucoidan") can be prepared from *Kjellmaniella crassifolia* and used in the present invention.

After the preparation of the fucoidans from *Kjellmaniella crassifolia*, U-fucoidan and F-fucoidan are separated by using an anionic exchange resin, a surfactant or the like. The existing ratio of U-fucoidan to F-fucoidan derived from *Kjellmaniella crassifolia* is about 1:2. U-fucoidan contains fucose, mannose, galactose, glucuronic acid and the like, and its sulfate content is about 20%. F-fucoidan contains fucose and galactose, and its sulfate content is about 50%. The molecular weight for both substances is distributed, centering about 200000 (*Summary of* 18*th Sugar Symposium*, p. 159, 1996).

U-fucoidan and F-fucoidan can be separated, for instance, by applying a fucoidan solution prepared from *Kjellmaniella crassifolia* onto DEAE-Cellulofine A-800 column, and carrying out elution by the concentration gradient technique using NaCl-containing buffer. One of the examples is shown in FIG. 1. Concretely, FIG. 1 is a diagram showing the separation of U-fucoidan and F-fucoidan, wherein the front peak in the figure is U-fucoidan, and the back peak is F-fucoidan.

As the acidic polysaccharide derived from Rhodophyceae, for instance, sulfated galactan, carrageenan, funoran, agaropectin or the like can be used. Also, agars and agarose derived from Rhodophyceae can be used in the present invention.

The Rhodophyceae include, for instance, *Gelidiun amansii*, Gracilaria, *Pteroclavia capillacae*, and the like.

As the acidic polysaccharide derived from Chlorophyceae, for instance, rhaman sulfate can be used. Chlorophyceae include, for instance, Ulva, Enteromorpha, Acetabularia, Chlorella and the like. Also, the acidic polysaccharide derived from Cyanophyceae such as Spirulina can be used in the present invention.

In the present invention, alginic acid, pectic acid, hyaluronic acid or the like itself can be used as the acidic polysaccharide which is the effective ingredient of the present invention. Further, a synthetic acidic polysaccharide prepared by adding, for instance, sulfate group to the above acidic polysaccharide can be also used. The synthetic acidic polysaccharide includes, for instance, synthetic acidic polysaccharides such as sulfates of cellulose, starch, mannan, xylan, alginic acid, pectin, pectic acid, hyaluronic acid, fructan, arabinan, chitin, pullulan, xyloglucan, dextran, and the like. Further, for instance, synthetic sulfated polysaccharides such as ribofuranan sulfate, xylofuranan sulfate, lentinan sulfate, curdlan sulfate, mannopyranan sulfate, sulfated starch and sulfated pectin, and synthetic sulfated alkyl polysaccharides such as a ribofuranan sulfate having palmitoyl group can be used. In addition, the highly-sulfated sulfated polysaccharide can be prepared by further sulfating the sulfated polysaccharide, and used as the synthetic acidic polysaccharide in the present invention. Each of these synthetic acidic polysaccharides can be prepared by a known method and used in the present invention. In addition, commercially available dextran sulfate and sulfated cellulose can be used in the present invention, and salts of these synthetic acidic polysaccharides may be used in the present invention.

These acidic polysaccharides may be prepared each by a known method. There can be used in the present invention a purified product of an acidic polysaccharide, an acidic polysaccharide-containing substance, or the like. As the acidic polysaccharide-containing substance, for instance, an acidic polysaccharide fraction derived from algae can be preferably used, and as the algae, the algae mentioned above can be preferably used as a raw material.

In addition, an acidic polysaccharide having low molecular weight obtained by degrading these acidic polysaccharides can be also used as the acidic polysaccharide of the present invention, as long as the acidic polysaccharide has an ability of maintaining or enhancing an antigen-specific cytotoxic activity of cytotoxic T cell.

Next, the acidic oligosaccharide and the acidic monosaccharide which can be used in the present invention are not particularly limited, as long as the acidic oligosaccharide and acidic monosaccharide have an ability of maintaining or enhancing an antigen-specific cytotoxic activity of cytotoxic T cell, and degradation products of the above acidic polysaccharides, synthetic acidic oligosaccharides and synthetic acidic monosaccharides can be used. In addition, the acidic oligosaccharide and the acidic monosaccharide are exemplified by, for instance, sulfated oligosaccharides and sulfated monosaccharides. Each of these sulfated oligosaccharide and sulfated monosaccharide can be prepared by sulfating each of the corresponding oligosaccharide or monosaccharide as a raw material by a known method. Also, salts of these sulfated oligosaccharide and sulfated monosaccharide can be preferably used. In addition, in the present invention, the acidic monosaccharide is exemplified by sulfated monosaccharides, for instance, a sulfated fucose, a sulfated glucose, a sulfated galactose, a sulfated xylose, a sulfated 2-deoxy-glucose, a sulfated mannose, a sulfated talose and the like. These sulfated monosaccharides may be prepared by a synthesis method, or prepared by degrading a sulfated polysaccharide obtained from a natural product and purifying the sulfated monosaccharide from the degradation product. In addition, the salts thereof can be prepared by a conventional method, and used in the present invention. In addition, as in the above-mentioned sulfated polysaccharides, a highly-sulfated sulfated oligosaccharide and a highly-sulfated sulfated monosaccharide can be prepared by further sulfating these sulfated oligosaccharides and sulfated monosaccharides, and can be used. Incidentally, in the present invention, the term "oligosaccharide" is defined as a saccharide compound in which 2 to 10 monosaccharides are connected, and the term "polysaccharide" is defined as a saccharide compound in which 11 or more monosaccharides are connected.

In addition, the degradation product of the acidic polysaccharide having an ability of maintaining or enhancing an antigen-specific cytotoxic activity of the cytotoxic T cell of the present invention can be prepared by a known method such as an enzymological method, a chemical method or a physical method, and degradation products having an ability of maintaining or enhancing an antigen-specific cytotoxic activity of the cytotoxic T cell can be selected and used.

Incidentally, the degradation product refers to those obtained by degrading an acidic polysaccharide, wherein the degradation product has a molecular weight of preferably from about 200 to about 100000, more preferably from about 1000 to about 30000, depending upon the acidic polysaccharide to be degraded.

Preferable methods for preparing the degradation product of the acidic polysaccharide used in the present invention include, for instance, an acid degradation method. By subjecting the acidic polysaccharide to an acid degradation, there can be prepared a degradation product having an ability of maintaining or enhancing a specific cytotoxic activity of cytotoxic T cell.

The conditions of the acid degradation for the acidic polysaccharide used in the present invention are not particularly limited, as long as the conditions enable to generate the degradation product having an ability of maintaining or enhancing a specific cytotoxic activity of cytotoxic T cell (hereinafter referred to as "degradation product of the present invention").

For instance, the acidic polysaccharide is dissolved or suspended in an aqueous solution of an acid or the like and subjected to an acid degradation reaction, thereby generating the degradation product of the present invention. Also, the reaction mixture may be heated during the reaction, thereby shortening the time period required for the generation of the degradation product of the present invention.

The kinds of the acid for dissolving or suspending the acidic polysaccharide are not particularly limited. There can be used an inorganic acid such as hydrochloric acid, sulfuric acid or nitric acid; an organic acid such as citric acid, formic acid, acetic acid, lactic acid or ascorbic acid; and a solid acid such as cationic exchange resin, cationic exchange fiber or cationic exchange membrane.

The concentration of the acid is not particularly limited, and the acid can be used at a concentration of preferably from 0.0001 to 5 N or so, more preferably from 0.01 to 1 N or so. In addition, the reaction temperature is not particularly limited, and the reaction temperature may be set at preferably from 0° to 200° C., more preferably from 20° to 130° C.

In addition, the reaction time is not particularly limited, and the reaction time may be set at preferably from several seconds to several days. The kinds and the concentration of the acids, the reaction temperature, and the reaction time may be properly selected depending upon the generated amount of the degradation product used in the present invention and the degree of polymerization of the degradation product. For instance, in the preparation of the degradation product of the fucoidan, it is preferable that an organic acid such as citric acid, lactic acid or malic acid is used, that the concentration of the acid is properly selected from the range of several dozens mM to several M, that the heating temperature in the range of from 50° to 110° C., more preferably from 70° to 95° C., and that the heating time in the range of from several minutes to 24 hours, whereby the degradation product of the present invention can be prepared. The acid degradation product of the fucoidan is exemplified by the acid degradation product of the fucoidan derived from *Kjellmaniella crassifolia*.

The degradation product of the present invention can be fractionated by using as an index its action for maintaining or enhancing specific cytotoxic activity of cytotoxic T cell. For instance, the acid degradation product can be subjected to a molecular weight fractionation by means of a gel filtration method, a fractionation method using a molecular weight fractionation membrane, or the like.

As an example of the gel filtration method, Cellulofine GCL-300 can be used to prepare any molecular weight fractions, for instance, one having a molecular weight exceeding 25000, one having a molecular weight of 25000 to exceeding 10000, one having a molecular weight of 10000 to exceeding 5000, one having a molecular weight of 5000 or less, and the like. Cellulofine GCL-25 can be used to prepare any molecular weight fractions from the fraction having a molecular weight of 5000 or less, for instance, one having a molecular weight of 5000 to exceeding 3000, one having a molecular weight of 3000 to exceeding 2000, one having a molecular weight of 2000 to exceeding 1000, one having a molecular weight of 1000 to exceeding 500, one having a molecular weight of 500 or less.

In addition, the molecular weight fractionation can be industrially carried out by using an ultrafiltration membrane. For instance, a fraction having a molecular weight of 30000 or less can be prepared by using FE10-FUS0382 manufactured by DAICEL CHEMICAL INDUSTRIES, LTD., or a fraction having a molecular weight of 6000 or less can be prepared by using FE-FUS-T653 manufactured by the same. Further, a fraction having a molecular weight of 500 or less can be obtained by using a nanofilter membrane. Any molecular weight fractions can be prepared by combining these gel filtration methods and molecular weight fractionation methods.

The degradation product of the acidic polysaccharide, for instance, a degradation product of the fucoidan, which can be used in the present invention is exemplified by the compound represented by the formula (I), the compound represented by the formula (II) and the compound represented by the formula (III), and these compounds can be prepared in accordance with the methods disclosed in WO 99/41288, WO 96/34004, and WO 00/50464. Incidentally, each of a fucoidan and an oligosaccharide having a repeating structure of the compound represented by the formula (I) as a basic backbone, a fucoidan and an oligosaccharide having a repeating structure of the compound represented by the formula (II) as a basic backbone, and a fucoidan and an oligosaccharide having a repeating structure of the compound represented by the formula (III) as a basic backbone can be also preferably used as the acidic polysaccharide and the acidic oligosaccharide of the present invention. Also, the degradation product of the acidic polysaccharide, for instance, the degradation product of the fucoidan, of the present invention is exemplified by the degradation product of the fucoidan described in WO 99/41288, WO 96/34004, and WO 00/50464.

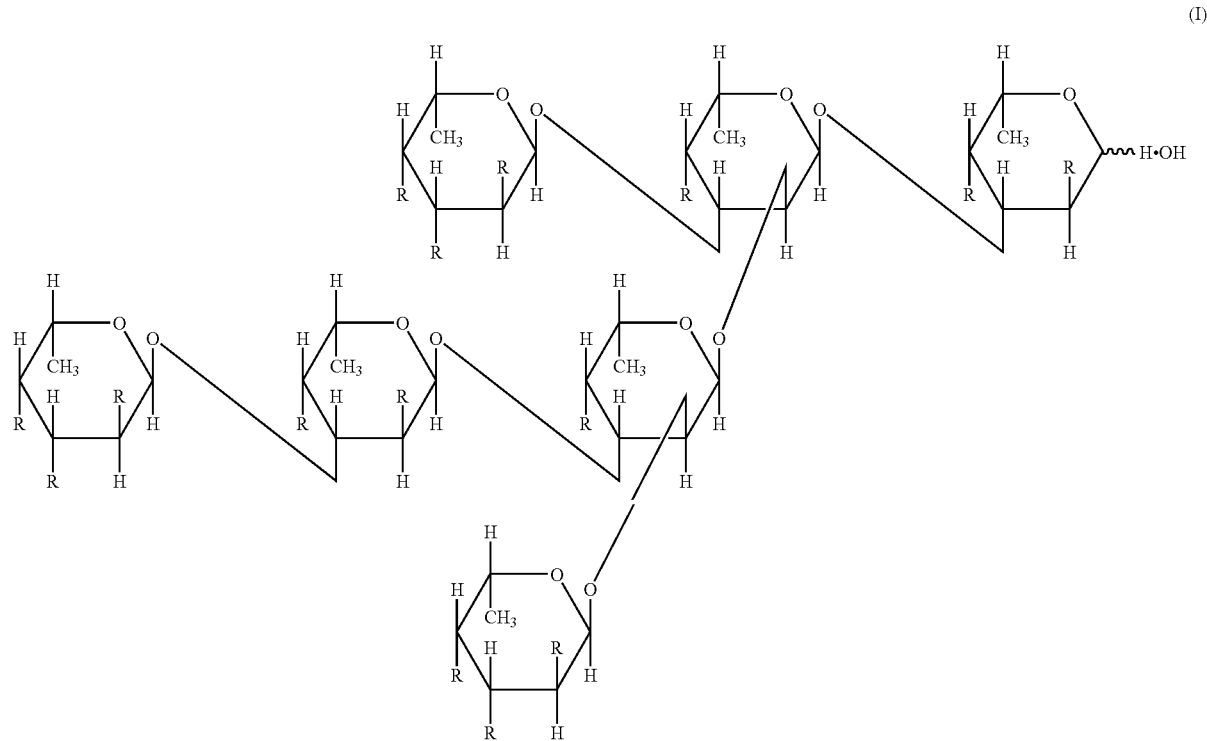

wherein R is OH or OSO$_3$H;

-continued

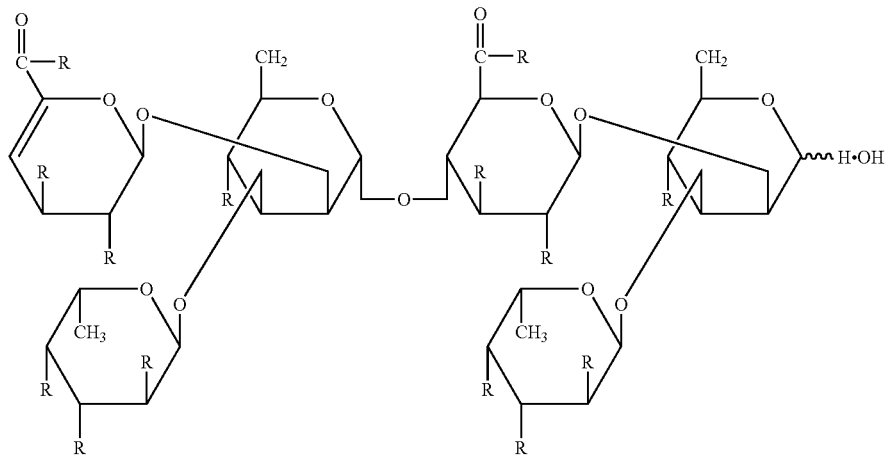

wherein R is OH or OSO₃H; and

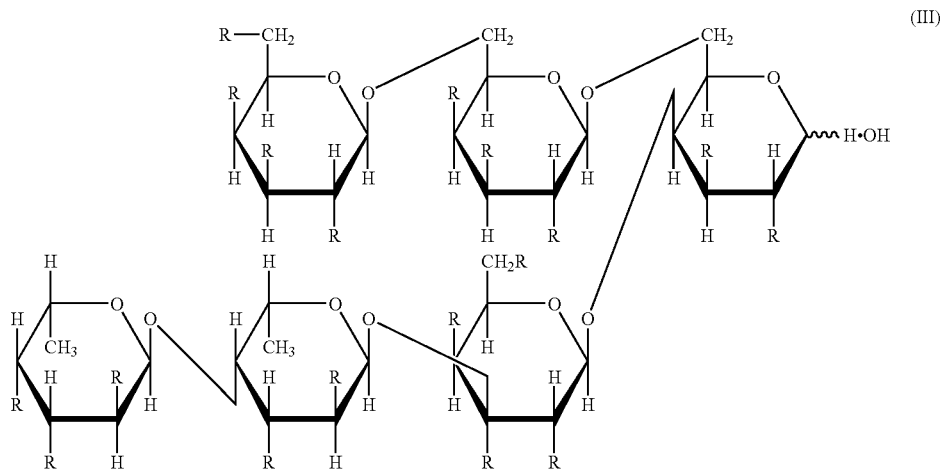

wherein R is OH or OSO₃H.

The compound represented by the formula (I) can be obtained by treating the previously mentioned F-fucoidan with endo-sulfated polysaccharide degrading enzyme (F-fucoidan-specific degradation enzyme) produced by Alteromonas sp. SN-1009 (FERM BP-5747), and purifying the degradation product. As to the content and the site of sulfate group in the compound, any ones can be purified from the degradation product. In addition, the polymer of the compound represented by the formula (I) is contained in the degradation product, and can be separated and purified depending on its purposes.

The compound represented by the formula (II) can be obtained by treating the previously mentioned U-fucoidan with endo-sulfated polysaccharide degrading enzyme (U-fucoidan-specific degradation enzyme) produced by Flavobacterium sp. SA-0082 (FERM BP-5402), and purifying the degradation product. As to the content and the site of sulfate group in the compound, any ones can be purified from the degradation product. In addition, the polymer of the compound represented by the formula (II) as a basic backbone is contained in the degradation product, and can be separated and purified depending on its purposes.

Incidentally, an example of the compound represented by the formula (I) includes a compound represented by the formula (IV) given below. Also, an example of the compound represented by the formula (II) includes a compound represented by the formula (VI) given below. Also, an example of the compound represented by the formula (III) includes a compound represented by the formula (V) given below.

The fucoidan derived from *Kjellmaniella crassifolia* is treated with F-fucoidan degradation enzyme produced by Alteromonas sp. SN-1009 (FERM BP-5747) and U-fucoidan degradation enzyme produced by Flavobacterium sp. SA-0082 (FERM BP-5402), and the resulting degradation product can be removed, to give a purified one of the above-mentioned G-fucoidan.

Flavobacterium sp. SA-0082 (FERM BP-5402) also produces endo-sulfated polysaccharide degrading enzyme specifically degrading G-fucoidan (G-fucoidan degradation enzyme). G-fucoidan is treated with the G-fucoidan degradation enzyme, thereby preparing degradation products of the G-fucoidan, and any ones can be purified from the degradation products depending on its purposes. The compound represented by the formula (III) is its example. As to the content and the site of sulfate group in the compound, any ones can be purified from the degradation product. In addition, the polymer of the compound represented by the formula (III) as a basic backbone is contained in the degradation products, and can be separated and purified depending on its purposes.

Incidentally, each of the enzyme described above is described in WO 97/26896 or WO 00/50464.

In addition, the fucoidan derived from *Kjellmaniella crassifolia* is heat-treated in the presence of an organic acid, whereby a polymer of glucuronic acid and mannose can be obtained, and the resulting polymer can be also used as an acidic polysaccharide having an ability of maintaining or enhancing an antigen-specific cytotoxic activity of the cytotoxic T cell of the present invention. Also, polymers having any polymerization degrees can be prepared by adjusting the heat treatment conditions and the heating time.

As described above, the effective ingredient used in the present invention is not particularly limited, as long as the effective ingredient has an action for maintaining or enhancing an antigen-specific cytotoxic activity of CTL. Various acidic polysaccharides, acidic oligosaccharides, acidic monosaccharides, and/or salts thereof can be used. Especially preferably, at least one compound selected from the group consisting of fucoidans, heparins, alginic acid, chondroitin sulfate A, chondroitin sulfate B, pectic acid, hyaluronic acid, degradation products of fucoidans, sulfated glucose, sulfated fucose and salts thereof can be used. In addition, in the present invention, the acidic polysaccharides which have been so far used as pharmaceuticals are preferably used. For instance, sodium dextran sulfate, hyaluronic acid, heparin and the like can be used. Sodium dextran sulfate is a sodium salt of sulfuric ester, obtained by sulfating a partially degraded product of dextran produced by fermentation of sucrose by Leuconostoc mesenteroides van Tieghem.

The salts of the acidic polysaccharide, the acidic oligosaccharide, and the acidic monosaccharide used in the present invention are not particularly limited, as long as the salts have an action for maintaining or enhancing an antigen-specific cytotoxic activity of CTL. The salts are exemplified by, for instance, alkali metal salts, alkaline earth metal salts, and salts with an organic base, including salts with, for instance, sodium, potassium, calcium, magnesium, or ammonium or salts of diethanolamine or ethylenediamine, and the like. These salts can be obtained, for instance, by converting an acidic group existing in the acidic polysaccharide, the acidic oligosaccharide, or acidic monosaccharide, for instance, sulfate group or carboxyl group existing in a fucoidan or the like, to a salt by a known method. It is preferable that the salts are pharmacologically acceptable salts.

The acidic polysaccharide, the acidic oligosaccharide, the acidic monosaccharide and/or the salts thereof, which are used as an effective ingredient in the present invention can be used alone or in admixture of two or more kinds. In addition, the derivatives of the effective ingredients, for instance, fatty acid derivatives thereof and the like, can be also used without any particular limitation, as long as they exhibit an ability of maintaining or enhancing a specific cytotoxic activity of CTL.

In the present invention, common conditions for incubating a precursor cell capable of differentiating to CTL together with an antigen-presenting cell (co-culturing) to induce CTL may be known conditions [see, for instance, the publication: Bednarek M. A. et al., *J. Immunology* 147 p.4047-4053 (1991)]. The conditions for co-culturing are not particularly limited, and the conditions usually used for cell culturing can be used. For instance, the cells can be cultured under the conditions of 37° C. in the presence of 5% $CO_2$, and the like. The co-culture is usually carried out for about 2 to about 15 days, during which time the antigen-presenting cell may be exchanged with freshly prepared one for restimulation. In addition, the medium can be exchanged with a fresh one at appropriate time intervals.

The content of the effective ingredient of the present invention in the medium used for the co-culture is not particularly limited, as long as the desired effect can be obtained. The content of the effective ingredient is preferably from 0.001 to 1000 µg/ml, more preferably from 0.01 to 100 µg/ml. Incidentally, it is preferable that the effective ingredient is dissolved in the medium.

The CTL thus induced has an ability of specifically recognizing the desired antigen, and, for instance, specifically destroy a cell having the antigen by its cytotoxic activity. This cytotoxic activity of CTL can be evaluated by a known method. For instance, the cytotoxic activity can be evaluated by determining cytotoxicity to a target cell labeled with the peptide presented by an antigen-presenting cell and a radioactive substance, a fluorescent substance or the like; an antigen-specific increase in CTL proliferation which can be determined by uptake of radioactivity; or the amount of cytokine such as GM-CSF or IFN-γ released antigen-specifically from CTL or target cell (see item (3) of Example 1-1 set forth below). Besides them, the cytotoxic activity can also be directly confirmed by using an antigenic peptide or complex labeled with a fluorescent pigment or the like. In this case, for instance, CTL is contacted with a first fluorescent marker coupled with a CTL specific antibody, and then with an antigenic peptide-MHC complex coupled with a second fluorescent marker, and the presence of a double-labeled cell is detected by FACS (fluorescence-activated cell sorting) analysis.

The CTL induced by the method of the present invention has an excellent property that the antigen-specific cytotoxic activity is not markedly lowered, as conventionally observed, even when the cell after induction is maintained or allowed to proliferate over a long period of time. Therefore, the induced CTL is cloned, whereby there can be also maintained the CTL as a lymphocyte having a stable cytotoxic activity. For instance, the induced CTL can be allowed to proliferate and expanded by stimulating the CTL with an antigen, various cytokines or anti-CD3 antibodies. It is preferable to use the method for maintaining or the method for expanding cytotoxic T cell of the present invention described below in the maintenance and expansion of the CTL.

The effects of the present invention described above can be confirmed by maintaining or expanding the CTL induced by the method of the present invention in an appropriate manner, and thereafter determining the cytotoxic activity by the method described above.

(2) Method for Maintaining Cytotoxic T Cell of Present Invention

The method for maintaining cytotoxic T Cell of the present invention is a method for maintaining CTL with keeping its antigen-specific cytotoxic activity. One of the great features of the method resides in that CTL is continuously cultured in a medium containing the effective ingredient of the present invention, whereby the antigen-specific cytotoxic activity of the cell can be continuously maintained.

The CTL which can be suitably used for the above-mentioned method is not limited, and CTL obtained by a known method can be maintained by the method of the present invention, with keeping its antigen-specific cytotoxic activity. In addition, the method is also preferably used for maintaining CTL obtained by the method for inducing cytotoxic T cell of the present invention described in the above item (1).

In the present invention, common conditions for continuously culturing CTL may be carried out in accordance with known conditions [see, for instance, the publication: Carter J. et al., *Immunology* 1986 Jan. 57 (1) p.123-129)]. The media used for the method for maintaining cytotoxic T cell of the present invention are not particularly limited, and for instance, the medium used for the above-mentioned method for inducing CTL can be used.

The method of the present invention is carried out by adding the above-mentioned effective ingredient to the medium. The content of the effective ingredient of the present invention in the medium for culturing is not particularly limited, as long as the desired effect can be obtained. The content of the effective ingredient is preferably from 0.001 to 1000 µg/ml, more preferably from 0.01 to 100 µg/ml. Incidentally, it is preferable that the effective ingredient is dissolved in the medium. In addition, the above-mentioned effective ingredient is preferably at least one compound selected from the group consisting of fucoidans, heparins, alginic acid, chondroitin sulfate A, chondroitin sulfate B, pectic acid, hyaluronic acid, degradation products of fucoidans, sulfated glucose, sulfated fucose and salts thereof. Further, cytokines or other known components can be added to the medium as desired. In the present invention, a medium containing IL-2 is preferably used. The culture conditions are not particularly limited, and the conditions used for ordinary cell culture can be used. For instance, the cells can be cultured under the conditions at 37° C. in the presence of 5% $CO_2$, and the like. In addition, the medium can be exchanged with a fresh one at appropriate time intervals.

As described above, CTL can be maintained with suppressing lowering of its specific cytotoxic activity by continuously culturing CTL in a medium containing the effective ingredient of the present invention. The effects of the present invention described above can be confirmed by determining the cytotoxic activity possessed by CTL maintained by the method of the present invention according to the method described in the above item (1). In addition, the CTL maintained by the method can be allowed to proliferate by a known expanding method, and the CTL thus proliferated also has a specific cytotoxic activity. Incidentally, as a method for expanding CTL, the method for expanding CTL of the present invention described below can be preferably used.

(3) Method for Expanding Cytotoxic T Cell of Present Invention

Cytotoxic T cell is cultured under appropriate conditions, whereby the cell count can be increased (expansion). Conventionally, several methods for expanding CTL have been developed. As a method capable of efficiently proliferating CTL in a short period of time, the above-mentioned REM method developed by Riddell et al. has been known. This method uses PBMC made non-proliferative by X ray irradiation (used as feeder cell) and EBV-transformed B cell (EBV-B cell) and comprises culturing CTL in the presence of IL-2 and an anti-CD3 monoclonal antibody. However, this method has been problematic in that risk of admixing EBV-B cell into T cell is not deniable.

The method for expanding cytotoxic T cell of the present invention is a method capable of increasing the cell count with keeping its antigen-specific cytotoxic activity. The method is characterized by incubating the cell (cultured) in the presence of the above-mentioned effective ingredient of the present invention.

In the method of the present invention, CTL which can be suitably used is not limited. The method can be suitably used for expansion of CTL obtained by a known method, CTL obtained by the method for inducing CTL of the present invention described in the above item (1), and CTL obtained by the method for maintaining CTL of the present invention described in the above item (2). Incidentally, in the present invention, common conditions for expanding CTL may be in accordance with known conditions [see, for instance, the publication: Uberi J. P. et al., *Clin. Immunol. Immunophathol.* 1994 Mar. 70 (3) p.234-240].

In the method for expanding cytotoxic T cell of the present invention, it is desired that CTL is cultured in a medium further containing an anti-CD3 antibody, preferably an anti-CD3 monoclonal antibody, in addition to the above-mentioned effective ingredient. In addition, more preferably, CTL is co-cultured with appropriate feeder cell.

The medium used for the above-mentioned method is not particularly limited. A known medium prepared by blending components necessary for culture or growth of CTL can be used, and may be, for instance, commercially available ones. Incidentally, in the case where CTL is co-cultured with feeder cell, it is desired that the medium is suitable for maintenance and growth of both the CTL and the feeder cell. These media may contain appropriate proteins, cytokines and other components in addition to the originally contained constituents. For instance, a medium containing IL-2 is preferably used in the present invention. An anti-CD3 antibody, especially an anti-CD3 monoclonal antibody, can be added for the purpose of activating T cell receptor on CTL. Incidentally, the content of the anti-CD3 antibody in the medium may be determined according to the known conditions. For instance, the content is preferably from 0.01 to 1 µg/ml.

The method for expanding CTL of the present invention is carried out by adding the above-mentioned effective ingredient to the medium. Incidentally, the above-mentioned effective ingredient is preferably at least one compound selected from the group consisting of fucoidans, heparins, alginic acid, chondroitin sulfate A, chondroitin sulfate B, pectic acid, hyaluronic acid, degradation products of fucoidans, sulfated glucose, sulfated fucose and salts thereof. In addition, the content of the effective ingredient of the present invention in the medium for culture is not particularly limited, as long as the desired effects can be obtained. The content of the effective ingredient is preferably from 0.001 to 1000 µg/ml, more preferably from 0.01 to 100 µg/ml. Incidentally, it is preferable that the effective ingredient is dissolved in the medium.

The feeder cell used for the method of the present invention is not particularly limited, as long as the feeder cell stimulates CTL cooperatively with an anti-CD3 antibody to activate T cell receptor. In the present invention, for instance, PBMC or EBV-B cell is used. Usually, a feeder cell is used after its proliferating ability is taken away by means of irradiation or the like. Incidentally, the content of the feeder cell in the medium may be determined according to the known conditions. For instance, the content is preferably from $1 \times 10^5$ to $1 \times 10^7$ cells/ml.

In a particularly preferred embodiment of the present invention, non-virus-infected cell, for instance, a cell other than EBV-B cell, is used as a feeder cell. By using the non-virus infected cell, the possibility that EBV is admixed in an expanded CTL can be eliminated, thereby making it possible to increase the safety in medical treatments utilizing CTL, such as adoptive immunotherapy.

In the method for expanding cytotoxic T cell of the present invention, the conditions for culture are not particularly limited, and the conditions used for usual cell culture can be used. For instance, the cell can be cultured under the conditions of 37° C. in the presence of 5% $CO_2$, and the like. In addition, the medium can be exchanged with a fresh one at appropriate time intervals.

The method for expanding CTL is not particularly limited ot a certain method, as long as the effective ingredient of the present invention is added to the medium used in the method. The present invention encompasses an embodiment of adding the effective ingredient of the present invention to a medium in conventional methods for expanding CTL other than the above-mentioned method.

According to the method for expansion of the present invention, for instance, CTL of which cell count is increased 100- to 1000-folds can be obtained by an expansion for 14 days. Further, CTL thus obtained has a higher antigen-specific cytotoxic activity, as compared to those obtained by a conventional method for expansion, for instance, the REM method.

The effects of the present invention as described above can be confirmed by determining the cytotoxic activity possessed by CTL expanded by the method of the present invention according to the method described in the above item (1).

In addition, the effective ingredient used in the present invention can be used as an agent for inducing CTL, an agent for maintaining CTL or an agent for expanding CTL (these agents are hereinafter referred to as an agent for culturing CTL), which acts for maintaining or enhancing an antigen-specific cytotoxic activity of CTL. The agent for culturing CTL may be the effective ingredient itself, or the agent for culturing CTL further comprises any other optional components, for instance, components necessary for culture or growth of CTL, feeder cell and the like, which are contained in the medium used in a method for inducing CTL, the medium used in a method for maintaining CTL or the medium used in a method for expanding CTL; appropriate proteins and cytokines (preferably IL-2); and other desired components. Also, a medium containing these agents for culturing CTL can be used as a medium for inducing, maintaining, or expanding CTL (these media are hereinafter referred to as a medium for CTL). These media optionally contain suitable components depending on the respective uses in addition to the basic constituents for cell culture and the above-mentioned compound. Incidentally, the agents for culturing CTL and the media for CTL mentioned above can be prepared by known methods.

Usually, in the CTL-containing culture obtained by using the method for inducing CTL, the method for maintaining CTL and the method for expanding CTL of the present invention described above, cells other than CTL such as helper T cell are admixed therein. In the present invention, the cells in the culture are collected from the culture by centrifugation or the like, and the cells can be directly used, for instance, as the CTL obtained by the method of the present invention.

In addition, a cell population (or a culture) rich in CTL having an antigen-specific cytotoxic activity can be further separated from the culture, and used as CTL obtained by the method of the present invention. Concretely, in the present invention, a cell population with a concentrated antigen-specific cytotoxic activity can be prepared by subjecting the culture to a separation procedure of CTL from cell other than the CTL (for instance, helper T cell) in the above-mentioned CTL-containing culture to use the cell population. The concentration of the antigen-specific cytotoxic activity by separating the above-mentioned cell population as described above could not have been accomplished by the conventional REM method. Therefore, as one embodiment of the present invention, there is provided a method for collecting cytotoxic T cell comprising the step of selecting a cell population rich in cytotoxic T cell having an antigen-specific cytotoxic activity from a CTL-containing culture obtained by any one of the method for inducing CTL, the method for maintaining CTL and the method for expanding CTL of the present invention. The method for collecting CTL of the present invention in a sense refers to a method of selectively obtaining a cell population of CTL having a high antigen-specific cytotoxic activity, and in a broad sense refers to a method for producing or acquiring a cell population of the CTL. The method of selecting the cell population is not particularly limited. For instance, the cell population rich in CTL can be obtained by selectively collecting only CTL from a CTL-containing culture obtained by using the method for inducing CTL, the method for maintaining CTL and the method for expanding CTL, using magnetic beads or a column to which an antibody against a cell surface antigen expressed on the CTL cell surface, for instance, an anti-CD8 antibody, is bound. CTL can be also selectively separated using a flow cytometer. The cell population rich in CTL can be obtained by removing cells other than CTL from a CTL-containing culture obtained by the method for inducing CTL, the method for maintaining CTL and the method for expanding CTL of the present invention. For instance, the cell population rich in CTL can be obtained by selectively removing helper T cell using magnetic beads or a column to which an antibody against a cell surface antigen expressed on helper T cell surface, for instance, an anti-CD3 antibody and an anti-CD4 antibody, is bound, in order to remove helper T cell from the culture. Also, a flow cytometer can be used for removing helper T cell. The cell population rich in CTL thus obtained has a more potent cytotoxic activity, as compared to a cell population collected non-selectively from a CTL-containing culture, so that it is more preferably used as the CTL obtained by the method of the present invention. In addition, in the present invention, the cell population rich in CTL also encompasses a cell population of CTL alone.

In addition, CTL can be further maintained or expanded according to the method for maintaining CTL or the method for expanding CTL of the present invention using the CTL obtained by the method for maintaining CTL or the method for expanding CTL of the present invention. Also, CTL having an even higher cytotoxic activity can be obtained by, for instance, obtaining a fraction rich in CTL according to the method described above from CTL obtained by the method for expansion of the present invention, and subjecting the fraction obtained to the method for expansion of the present invention. In addition, CTL obtained by the method for expansion of the present invention can maintain its cytotoxic activity by using the method for maintaining CTL of the present invention.

Further, the present invention provides CTL obtained by the method for inducing CTL, the method for maintaining CTL and the method for expanding CTL of the present invention mentioned above. All of the above-mentioned CTLs have an antigen-specific cytotoxic activity, in which there is little lowering of cytotoxic activity, even when the CTL is subjected to the continuous culture or expansion over a long period of time. In addition, the present invention provides a therapeutic agent comprising the CTL as an effective ingredient. The therapeutic agent is especially suitably used in adoptive immunotherapy. In the adoptive immunotherapy, CTL having an antigen-specific cytotoxic activity suitable for treating a patient is administered to the patient by, for instance, intravenous administration. The therapeutic agent can be prepared by, for instance, blending the CTL prepared by the method of the present invention as an effective ingredient with, for instance, a known organic or inorganic carrier, an excipient, a stabilizing agent and the like which are suitable for parenteral administration, according to a method known in the pharmaceutical field. As the CTL, CTL prepared by the method for expanding CTL of the present invention without using EBV-infected cell is especially preferable for this purpose. Incidentally, various conditions for the therapeutic agent, such as the content of CI L in the therapeutic agent and the dosage of the therapeutic agent, can be appropriately determined according to the known adoptive immunotherapy.

The present invention will be more concretely described by means of the examples, without by no means limiting the scope of the present invention thereto. Unless specified otherwise, "%" in Examples means "% by weight."

PREPARATION EXAMPLE 1

*Kjellmaniella crassifolia* was sufficiently dried, and thereafter 20 kg of the dried product was powdered with a free mill (manufactured by Nara Kikai Seisakusho). In 900 liters of tap water was dissolved 7.3 kg of calcium chloride dihydrate (manufactured by Nippon Soda Co., Ltd.), and 20 kg of the powdered product of *Kjellmaniella crassifolia* was then mixed therewith. The resulting mixture was heated for 40 minutes by blowing steam until the liquid temperature was raised from 12° to 90° C. Thereafter, the mixture was kept at 90° to 95° C. for 1 hour under stirring, and then cooled, to give 1100 liters of a cooled product. Subsequently, the cooled product was subjected to solid-liquid separation with a solid-liquid separator (manufactured by West Farrier Separator, Model: CNA), to give about 900 liters of supernatant after solid-liquid separation. The amount 360 liters of the supernatant after solid-liquid separation was concentrated up to a volume of 20 liters with FE10-FC-FUS0382 (fraction molecular weight: 30000) manufactured by DAICEL CHEMICAL INDUSTRIES, LTD. Thereafter, the steps of adding 20 liters of tap water and again concentrating the resulting liquid mixture up to a volume of 20 liters were repeated 5 times, and the concentrate was subjected to a desalting treatment, to give 25 liters of an extract derived from *Kjellmaniella crassifolia*. One liter of the extract was lyophilized, to give 13 g of a dried product of a fucoidan derived from *Kjellmaniella crassifolia*.

PREPARATION EXAMPLE 2

Seven grams of the dried product of the fucoidan described in Preparation Example 1 was dissolved in 700 ml of a 20 mM imidazole buffer (pH 8) containing 50 mM sodium chloride and 10% ethanol, and insoluble substances were removed by centrifugation. The supernatant after centrifugation was applied onto a DEAE-Cellulofine A-800 column (φ 11.4 cm×48 cm) (manufactured by Seikagaku Corporation) equilibrated with the same buffer, and then washed with the same buffer. The elution was carried out with a concentration gradient of from 50 mM to 1.95 M sodium chloride (250 ml per fraction). A total sugar content and an uronic acid content were determined by the phenol-sulfuric acid method and the carbazole-sulfuric acid method, to give Fractions 43 to 49, Fractions 50 to 55, and Fractions 56 to 67, in the order of elution. Next, these fractions were desalted by electrodialysis, and thereafter lyophilized, to give each of Fraction I (340 mg) from Fractions 43 to 49, Fraction II (870 mg) from Fractions 50 to 55, and Fraction III (2.64 g) from Fractions 56 to 67. FIG. 1 shows an elution pattern of the fucoidan derived from *Kjellmaniella crassifolia* on the DEAE-Cellulofine A-800 column. In FIG. 1, the axis of ordinates is the absorbance at 530 nm as determined by the carbazole-sulfuric acid method (solid circles in the figure), the absorbance at 480 nm as determined by the phenol-sulfuric acid method (open circles in the figure), and the electric conductivity (mS/cm: open squares in the figure), and the axis of abscissas is the fraction number. In the figure, the front peak shows U-fucoidan, and the back peak shows F-fucoidan.

PREPARATION EXAMPLE 3

(1) A 2-liter Erlenmeyer flask was charged with 600 ml of a culture medium comprising an artificial sea water (manufactured by Jamarin Laboratory), pH 8.2, containing 0.25% glucose, 1.0% peptone, and 0.05% yeast extract, and then sterilized (at 120° C. for 20 minutes). Alteromonas sp. SN-1009 (FERM BP-5747) was inoculated into the culture medium, and cultured at 25° C. for 26 hours, to give a seed culture medium. A 30-liter jar fermentor was charged with 20 liters of a culture medium comprising an artificial sea water, pH 8.0, containing 1.0% peptone, 0.02% yeast extract, 0.2% sulfated polysaccharide described in item (2) of Example 2 described below, and 0.01% defoaming agent (manufactured by Shin-Etsu Chemical Co., Ltd., KM70), and sterilized at 120° C. for 20 minutes. After cooling, a 30 L jar fermentor was charged with 600 ml of the above-mentioned seed culture medium, and cultured at 24° C. for 24 hours under the conditions of 10 liters of aeration per minute and a stirring rate of 250 rpm. After termination of the culture, the culture medium was centrifuged, to give cells and culture supernatant. This culture supernatant was concentrated with an ultrafilter equipped with holofiber having an excluding molecular weight of 10000, and the concentrate was then subjected to salting out with an 85% saturated ammonium sulfate. Precipitates formed were harvested by centrifugation, and sufficiently dialyzed against a 20 mM Tris-HCl buffer (pH 8.2) containing an artificial sea water at a one-tenth concentration, to give 600 ml of a solution of an F-fucoidan degradation enzyme, selectively acting on the F-fucoidan.

(2) Two kilograms of dried *Kjellmaniella crassifolia* was powdered with a cutter mill (manufactured by Masuko Sangyo) fitted with a screen having a diameter of 1 mm, and the resulting seaweed chips were suspended in 20 liters of 80% ethanol. The suspension was stirred at 25° C. for 3 hours and filtered with a filter paper, and thereafter the residue was sufficiently washed. The residue obtained was suspended in 40 liters of a 20 mM sodium phosphate buffer, pH 6.5, which was heated to 95° C., the buffer containing 50 mM sodium chloride. The suspension was treated at 95° C. for 2 hours with occasional stirring, to extract a sulfated polysaccharide.

The suspension of the extract was filtered, to give a filtrate. Thereafter, the filtration residue was washed with 3.5 liters of 100 mM sodium chloride, to give an additional filtrate.

Both filtrates were combined, and then the temperature was lowered to 30° C. After 3000 U of alginic acid lyase (manufactured by Nagase Seikagaku Kogyo) was added to the resulting mixture, 4 liters of ethanol was added thereto. The resulting mixture was stirred at 25° C. for 24 hours. Next, the mixture was centrifuged, and the resulting supernatant was concentrated up to a volume of 4 liters with an ultrafilter equipped with holofiber having an excluding molecular weight of 100000. Further, the ultrafiltration was continued with 100 mM sodium chloride containing 10% ethanol until a colored substance was no longer filtered.

Precipitates formed in a non-filtrate solution were removed by centrifugation, and the temperature of the resulting supernatant was lowered to 5° C. The pH was adjusted to 2.0 with 0.5 N hydrochloric acid, and thereafter the formed precipitates such as a protein were removed by centrifugation. The pH of the resulting supernatant was rapidly adjusted to 8.0 with 1 N sodium hydroxide.

Next, an ultrafiltration was carried out with an ultrafilter equipped with holofiber having an excluding molecular weight of 100000, and the solvent was completely substituted with 20 mM sodium chloride, pH 8.0. Thereafter, the pH was again adjusted to 8.0, and the resulting mixture was centrifuged and then lyophilized, to give about 95 g of a sulfated polysaccharide.

(3) Two kilograms of dried *Kjellmaniella crassifolia* was powdered with a cutter mill fitted with a screen having a diameter of 1 mm, and the resulting seaweed chips were suspended in 20 liters of 80% ethanol. The resulting suspension was stirred at 25° C. for 3 hours, and filtered with a filter paper, and thereafter the residue was sufficiently washed. The residue obtained was suspended in 20 liters of a buffer (pH 8.2) containing 30 ml of a solution of the F-fucoidan degradation enzyme prepared in item (1) of the above-mentioned Preparation Example 3, 10% ethanol, 100 mM sodium chloride, 50 mM calcium chloride and 50 mM imidazole, and the resulting mixture was stirred at 25° C. for 48 hours. This suspension was filtered with a stainless screen having a screen-opening diameter of 32 μm, and the residue was washed with 10% ethanol containing 50 mM calcium chloride. Further, the residue was suspended in 10 liters of 10% ethanol containing 50 mM calcium chloride, and the suspension was stirred for 3 hours, and thereafter filtered with the stainless screen, and the residue was washed. Further, the residue was suspended under the same conditions, and the suspension was then stirred for 16 hours. The suspension was filtered with the stainless screen having a diameter of 32 μm, and the residue was washed.

The filtrate and the washings thus obtained were collected, and the combined mixture was subjected to ultrafiltration with an ultrafilter equipped with holofiber having an excluding molecular weight of 3000, thereby separating a filtered solution from a non-filtered solution.

This filtered solution was concentrated to a volume of about 3 liters with a rotary evaporator, and thereafter the concentrate was centrifuged, to give supernatant. The supernatant obtained was desalted with an electrodialyzer equipped with a membrane having an excluding molecular weight of 300. To the resulting solution was added calcium acetate so as to give a concentration of 0.1 M, and precipitates formed were removed by centrifugation. The resulting supernatant was applied onto a DEAE-Cellulofine column (amount of resin: 4 liters) previously equilibrated with 50 mM calcium acetate, and sufficiently washed with 50 mM calcium acetate and 50 mM sodium chloride. Thereafter, the elution was carried out with a concentration gradient of from 50 mM to 800 mM sodium chloride. The eluate at this time was collected 500 ml each. The collected fraction was analyzed by cellulose acetate membrane electrophoresis [*Analytical Biochemistry*, 37, 197-202 (1970)]. As a result, a sulfated saccharide which was eluted on a concentration of about 0.4 M sodium chloride (proximity of Fraction No. 63) was homogeneous.

Then, a solution of Fraction No. 63 was first concentrated to a volume of 150 ml, and thereafter sodium chloride was added so as to give a concentration of 4 M. The resulting solution was applied onto a Phenyl-Cellulofine column (amount of resin: 200 ml) previously equilibrated with 4 M sodium chloride, and sufficiently washed with 4 M sodium chloride. Non-adsorbent sulfated saccharide fractions were collected, and desalted with an electrodialyzer equipped with a membrane having an excluding molecular weight of 300, to give 505 ml of a desalted solution.

Forty milliliters of the desalted solution obtained was applied onto a Cellulofine GCL-90 column (4.1 cm×87 cm) equilibrated with 0.2 M sodium chloride containing 10% ethanol, to perform gel filtration. The collection was performed at 9.2 ml per fraction.

All of the fractions were analyzed for a total sugar content by the phenol-sulfuric acid method [*Analytical Chemistry*, 28, 350 (1956)].

As a result, since the sulfated saccharide formed a single peak, Fraction Nos. 63 to 70, which were fractions corresponding to a central part of the peak were collected. The combined fraction was desalted with an electrodialyzer equipped with a membrane having an excluding molecular weight of 300, and thereafter lyophilized, to give 112 mg of a dried product of the compound represented by the following formula (IV). The compound is hereinafter referred to as 7-12SFd-F.

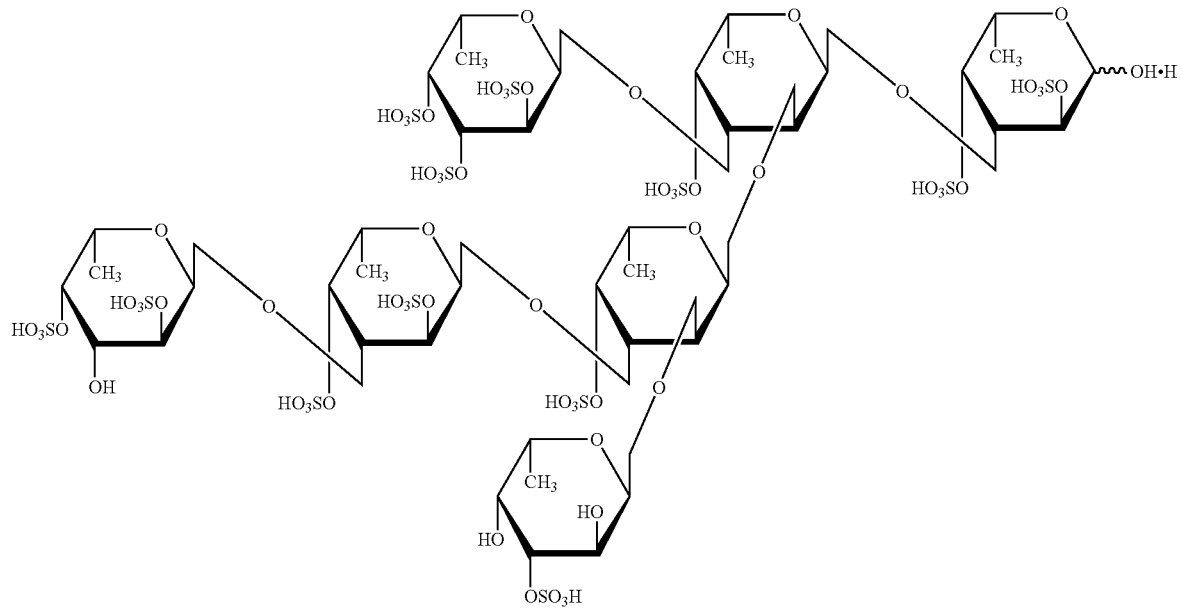

(4) To 80 ml of a 2.5% aqueous solution of Fraction III (F-fucoidan) prepared in Preparation Example 2 were added 16 ml of a 1 M Tris-HCl buffer (pH 7.6), 16 ml of a 1 M aqueous $CaCl_2$ solution, 24 ml of a 4 M aqueous NaCl solution, 8 ml of the solution of the F-fucoidan degradation enzyme obtained in item (1) of Example 3 and 176 ml of distilled water, and the resulting mixture was heated at 30° C. for 3 hours. The resulting enzymatically treated F-fucoidan solution was concentrated with a rotary evaporator so as to give a final concentration of the enzymatically treated F-fucoidan of 2%, and thereafter the concentrate was dialyzed in distilled water, to give a 2% aqueous solution of the enzymatically treated F-fucoidan. This sample was analyzed by HPLC (column: SB802.5; column temperature: 35° C.; mobile phase: 50 mM NaCl; flow rate: 0.5 ml/min; detection: RI ATT=8). As a result, it was revealed that about 40% of the sample was 7-12SFd-F as shown by the formula (IV).

PREPARATION EXAMPLE 4

(1) Two kilograms of dried *Kjellmaniella crassifolia* was powdered with a cutter mill (manufactured by Masuko Sangyo) fitted with a screen having a hole diameter of 1 mm. After the powdered product was stirred in 20 liters of 80% ethanol at 25° C. for 3 hours, the mixture was filtered, and the residue was washed. The resulting residue was suspended in 20 liters of a 30 mM imidazole buffer (pH 8.2) containing 50 mM calcium chloride, 100 mM sodium chloride, 10% ethanol, and 1 U of Alteromonas sp. SN-1009 (FERM BP-5747) F-fucoidan degradation enzyme prepared in item (1) of Preparation Example 3. The resulting suspension was stirred at 25° C. for 2 days, and thereafter filtered with a stainless screen having a hole diameter of 32 μm, and the residue was washed. The resulting residue was suspended in 40 liters of a sodium phosphate buffer (pH 6.6) containing 100 mM sodium chloride, 10% ethanol and 4 g of an alginic acid lyase (manufactured by Nagase Seikagaku Kogyo). The resulting suspension was stirred at 25° C. for 4 days, and thereafter centrifuged, to give supernatant. In order to remove low-molecular weight products of alginic acid contained in the supernatant obtained, the supernatant was concentrated to a volume of 2 liters with an ultrafilter equipped with holofiber having an excluding molecular weight of 100000, and thereafter the solvent was exchanged for 100 mM sodium chloride containing 10% ethanol. To the resulting solution was added with stirring an equivolume of 400 mM calcium acetate, and thereafter the mixture was centrifuged. The pH of the resulting supernatant was adjusted to 2 with 1 N hydrochloric acid, with cooling on ice. Precipitates formed were removed by centrifugation, and the pH of the resulting supernatant was adjusted to 8.0 with 1 N sodium hydroxide. This solution was concentrated to a volume of 1 liter by ultrafiltration, and thereafter the solvent was exchanged for 100 mM sodium chloride. Precipitates formed at this time were removed by centrifugation. In order to remove hydrophobic substances in the resulting supernatant, sodium chloride was added to the supernatant so as to give a concentration of 1 M, and the resulting mixture was applied onto a column containing 3 liters of Phenyl-Cellulofine (manufactured by Seikagaku Corporation) equilibrated with 1 M sodium chloride, to collect an effluent fraction. The fraction was concentrated with an ultrafilter, and thereafter the solvent was exchanged for 20 mM sodium chloride. The resulting solution was lyophilized, and the weight of the lyophilized product was 29.3 g.

(2) Fifteen grams of the above-mentioned lyophilized product was dissolved in 1.5 liters of 50 mM Tris-HCl buffer containing 400 mM sodium chloride and 9 U of an endo-sulfated polysaccharide-degrading enzyme (U-fucoidan degradation enzyme) obtained from a culture prepared by culturing Flavobacterium sp. SA-0082 (FERM BP-5402) disclosed in WO97/26896. After the resulting solution was subjected to the reaction at 25° C. for 6 days, the reaction mixture was concentrated to a volume of about 300 ml with an evaporator. The concentrate was placed in a dialysis tube having an excluding molecular weight of 3500 and thoroughly dialyzed. The solution remaining in the dialysis tube was applied onto a column containing 4 liters of DEAE-Cellulofine A-800 equilibrated with 50 mM sodium chloride, and sufficiently washed with 50 mM sodium chloride. Thereafter, the elution was carried out on a concentration gradient of from 50 to 650 mM sodium chloride. Further, the elution was sufficiently carried out in the same column with 650 mM sodium chloride. Among the eluted fractions, the fractions eluted with 650 mM sodium chloride were collected as a sulfated fucogalactan fraction, and concentrated with an ultrafilter having an excluding molecular weight of 100000. Thereafter, the solvent was substituted with 10 mM sodium chloride, and the resulting solution was lyophilized, to give 0.85 g of a lyophilized product of sulfated fucogalactan. The sulfated fucogalactan obtained (G-fucoidan) was found to contain galactose and fucose as constituting saccharides in a molar ratio of about 2:1.

(3) For the production of G-fucoidan degradation enzyme, 600 ml of a culture medium comprising an artificial sea water (manufactured by Jamarin Laboratory), pH 7.5, containing 0.1% glucose, 1.0% peptone, and 0.05% yeast extract was sterilized at 120° C. for 20 minutes, and thereafter Flavobacterium sp. SA-0082 (FERM BP-5402) was inoculated into the culture medium and cultured at 24° C. for 23 hours, to give a seed culture medium. A 30-liter jar fermentor was charged with 20 liters of a culture medium comprising an artificial sea water (pH 7.5) containing 0.2% fucoidan fraction derived from Kjellmaniella crassifolia prepared by the method of item (1) of Example 4, 2.0% peptone, 0.01% yeast extract, and 0.01% defoaming agent (manufactured by Shin-Etsu Chemical Co., Ltd., KM70), and sterilized at 120° C. for 20 minutes. After cooling, 600 ml of the above-mentioned seed culture medium was inoculated, and cultured at 24° C. for 23 hours under the conditions of 10 liters of aeration per minute and a stirring rate of 125 rotations per minute. After termination of the culture, the culture medium was centrifuged, to give cells.

The cells obtained were suspended in 1200 ml of a 10 mM Tris-HCl buffer (pH 8.0) containing 0.4 M sodium chloride, and subjected to ultrasonic disruption. Thereafter, the resulting product was centrifuged, to give a cell extract. The cell extract obtained was sufficiently dialyzed against the same buffer, and centrifuged, to give supernatant. To the resulting supernatant was added ammonium sulfate so as to give a final concentration of 90% saturation, and precipitates formed were collected by centrifugation. The precipitates obtained were dissolved in 150 ml of a 10 mM Tris-HCl buffer (pH 8.0) containing 50 mM sodium chloride. The resulting solution was sufficiently dialyzed against the same buffer, and centrifuged. The supernatant obtained was applied onto a 500-mL DEAE-Sepharose FF column (manufactured by Amersham-Pharmacia) equilibrated with the same buffer, and washed with the same buffer. Thereafter, the elution was carried out with a concentration gradient of from 50 mM to 600 mM sodium chloride, to collect an active fraction.

The active fraction obtained was sufficiently dialyzed against a 10 mM Tris-HCl buffer (pH 8.0) containing 0.1 M sodium chloride, applied onto a column containing 100 mL of DEAE-Cellulofine A-800 (manufactured by Seikagaku Corporation) equilibrated with the same buffer, and washed with the same buffer. Thereafter, the elution was carried out with a concentration gradient of from 0.1 M to 0.4 M sodium chloride, to collect an active fraction. Sodium chloride was added to the resulting active fraction so as to give a concentration of 4 M. The solution obtained was applied onto a column containing 20 mL of Phenyl-Cellulofine (manufactured by Seikagaku Corporation) equilibrated with a 10 mM Tris-HCl buffer (pH 8.0) containing 4 M sodium chloride, and washed with the same buffer. Thereafter, the elution was carried out with a concentration gradient of from 4 M to 1 M sodium chloride. Subsequently, a sufficient elution was further carried out with a 10 mM Tris-HCl buffer (pH 8.0) containing 1 M sodium chloride, to collect an active fraction. Sodium chloride was added to the active fraction obtained so as to give a concentration of 3 M. The resulting solution was applied onto a column containing 10 mL of Phenyl-Cellulofine (manufactured by Seikagaku Corporation) equilibrated with a 10 mM Tris-HCl buffer (pH 8.0) containing 3 M sodium chloride, and washed with the same buffer. Thereafter, the elution was carried out with a concentration gradient of from 3 M to 0.5 M sodium chloride. Subsequently, a sufficient elution was further carried out with a 10 mM Tris-HCl buffer (pH 8.0) containing 0.5 M sodium chloride, to collect an active fraction. The purified enzyme thus obtained was used as G-fucoidan degradation enzyme.

(4) G-fucoidan described in item (2) of Preparation Example 4 was treated with the above purified G-fucoidan degradation enzyme, to prepare a low-molecular weight product. Specifically, 1.94 g of G-fucoidan was dissolved in a 25 mM Tris-HCl buffer (pH 8.0) containing 0.2 M sodium chloride. Thereafter, 186 mU of G-fucoidan degradation enzyme was added thereto, and the resulting solution was subjected to the reaction at 25° C. for 6 days. The reaction mixture was concentrated to a volume of 80 ml with an evaporator. The concentrate was applied onto a Cellulofine GCL-1000 column (4×90 cm) (manufactured by Seikagaku Corporation) for molecular weight fractionation. The fractions having a molecular weight of 15000 or less were collected, and the combined fraction is referred to as a G-fucoidan degradation enzyme-digested fraction.

(5) The above G-fucoidan enzyme-digested fraction was concentrated to a volume of 500 ml with an evaporator, and thereafter the concentrate was desalted with an electrodialyzer. The resulting desalted product was applied onto a column containing 1 liter of DEAE-Cellulofine A-800 (manufactured by Seikagaku Corporation) previously equilibrated with a 10 mM imidazole-hydrochloric acid buffer (pH 8) containing 10 mM sodium chloride, and washed with the same buffer. Thereafter, the elution was carried out with a concentration gradient of from 10 mM to 900 mM sodium chloride. The eluate was collected 61 ml each, and each of its sugar content was determined by the phenol-sulfuric acid method. The fractions eluted with proximity of 270 mM sodium chloride were collected since they formed a peak of sugar content, and the combined fraction is referred to as 270 mM-eluted fraction (ii).

In addition, to the above-mentioned 270 mM-eluted fraction (ii) was added water so as to have the same electric conductivity as that of a 10 mM imidazole-hydrochloric acid buffer (pH 8) containing 150 mM sodium chloride, and the resulting solution was applied onto a column containing 200 ml of DEAE-Cellulofine A-800 (manufactured by Seikagaku Corporation) previously equilibrated with a 10 mM imidazole-hydrochloric acid buffer (pH 8) containing 150 mM sodium chloride and washed with the same buffer. Thereafter, the elution was carried out with a concentration gradient of from 150 mM to 300 mM sodium chloride. The eluate was collected 12 ml each, and each of its sugar content was determined by the phenol-sulfuric acid method. Fractions eluted with proximity of from 160 mM to 180 mM sodium chloride were collected, and concentrated to a volume of 2 ml with a speed vac (manufactured by SAVANT Instruments Inc.). Thereafter, the concentrate was applied onto a column containing 200 ml of Cellulofine GCL-25 (manufactured by Seikagaku Corporation) previously equilibrated with 10% ethanol solution, and the elution was carried out with the same solution. The eluate was collected 2 ml each, and each of its sugar content was determined by the phenol-sulfuric acid method. Fractions forming a peak of sugar content were collected, and referred to as (D).

The above Fraction (D) was desalted with an electrodialyzer, and thereafter lyophilized. The composition of sugars and the molecular weight were analyzed. In addition, the structural analysis was carried out by NMR analysis after substitution with heavy water by a prescribed method.

Properties of (D)

Molecular weight; 1358

$^1$H-NMR (D$_2$O)

δ; 5.19 (1H, d, J=4.3 Hz, F1-1-H), 4.93 (1H, d, J=3.7 Hz, F2-1-H),
4.62 (1H, overlapped with HOD, G1-1-H), 4.59 (1H, overlapped with HOD,
G2-1-H), 4.54 (1H, d-d, J=10.6, 2.7 Hz, F1-3-H), 4.46 (1H, d, J=7.6 Hz,
G3-1-H), 4.46 (1H, m, F2-3-H), 4.41 (1H, br-s, G2-4-H), 4.41 (1H, d, J=7.6 Hz,
G4-1-H), 4.37 (1H, q, J=6.4 Hz, F2-5-H), 4.27 (1H, m, G2-3-H), 4.24 (1H, br-s,
G3-4-H), 4.21 (1H, m, G3-3-H), 4.19 (1H, m, G4-3-H), 4.15 (1H, br-s,
G4-4-H), 4.13 (1H, q, J=6.7 Hz, F1-5-H), 4.09 (1H, d, J=2.7 Hz, F1-4-H),
4.04 (1H, d, J=2.8 Hz, F2-4-H), 3.98 (1H, m, G2-6-H), 3.96 (1H, d-d, J=10.6,
4.3 Hz, F1-2-H), 3.93 (1H, m, G3-6-H), 3.88 (1H, br-s, G1-4-H), 3.86 (1H, m,
G2-5-H), 3.81 (1H, m, G2-6-H), 3.81 (1H, m, F2-2-H), 3.80 (1H, m,
G3-5-H), 3.80 (1H, m, G3-6-H), 3.66 (1H, m, G1-3-H), 3.65 (1H, m,
G2-2-H), 3.64 (1H, m, G1-6-H), 3.64 (1H, m, G4-6-H), 3.61 (1H, m,
G4-5-H), 3.58 (1H, m, G1-2-H), 3.56 (1H, m, G1-6-H), 3.56 (1H, m,
G4-6-H), 3.55 (1H, m, G4-2-H), 3.54 (1H, m, G1-5-H), 3.54 (1H, m,
G3-2-H), 1.20 (3H, d, J=6.7,F1-6-H), 1.14 (3H, d, J=6.4,F2-6-H)

Composition of sugars: L-fucose: D-galactose =2:4 (molar ratio)

Sulfate group: 5 molecules

Here, the numbers assigned to the peaks in the $^1$H-NMR are as show in 5 the following formula (V). The compound is hereinafter referred to as 6-5SFd-G.

PREPARATION EXAMPLE 5

One-hundred and twenty grams of the sulfated polysaccharide prepared in item (2) of Preparation Example 3 was suspended in 8 liters of a 20 mM imidazole buffer (pH 7.5) containing 20 mM calcium chloride, 300 mM sodium chloride, 10% ethanol and 10 U of the F-fucoidan degradation enzyme prepared in item (1) of Preparation Example 3. The resulting suspension was stirred at 25° C. for 3 days, and subjected to an ultrafiltration with an ultrafilter equipped with holofiber having an excluding molecular weight of 100000, with adding the above-mentioned buffer.

The U-fucoidan degradation enzyme described in item (2) of Preparation Example 4 was added to the ultrafiltrate, and the resulting mixture was stirred at 25° C. for 2 days and subjected to an ultrafiltration with an ultrafilter equipped with holofiber having an excluding molecular weight of 100000, with adding water.

The filtrate was collected, and concentrated to a volume of 1.5 liters with an evaporator. Thereafter, the concentrate was completely desalted with a desalting apparatus, applied onto a column containing 3 liters of DEAE-Cellulofine A-800 previously equilibrated with 5 mM imidazole-hydrochloric acid buffer (pH 6.5) containing 30 mM sodium chloride, and washed with 6 liters of the same buffer. Thereafter, the elution was carried out with a concentration gradient of from 30 mM to 500 mM sodium chloride. The amount of the solution required for the elution was 48 liters. The eluate was collected 180 ml each, and each sugar content was determined by the phenol-sulfuric acid method. In addition, the absorbance at 232 nm was determined at the same time. The fractions eluted with 130 mM to 170 mM sodium chloride were collected since they formed a single peak. The combined fraction was desalted with a desalting apparatus, and thereafter lyophilized, to give 5.85 g of an oligosaccharide. It was confirmed that this oligosaccharide has a molecular weight of 1128 by mass spectrometry, and that it is the compound represented by the following formula (VI) by NMR analysis. The compound is hereinafter referred to as 6-2SFd-U.

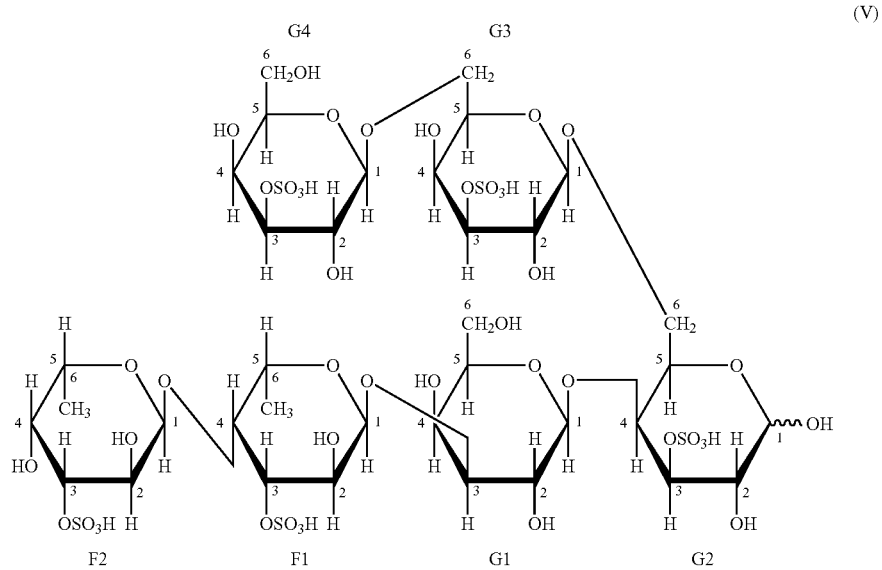

(V)

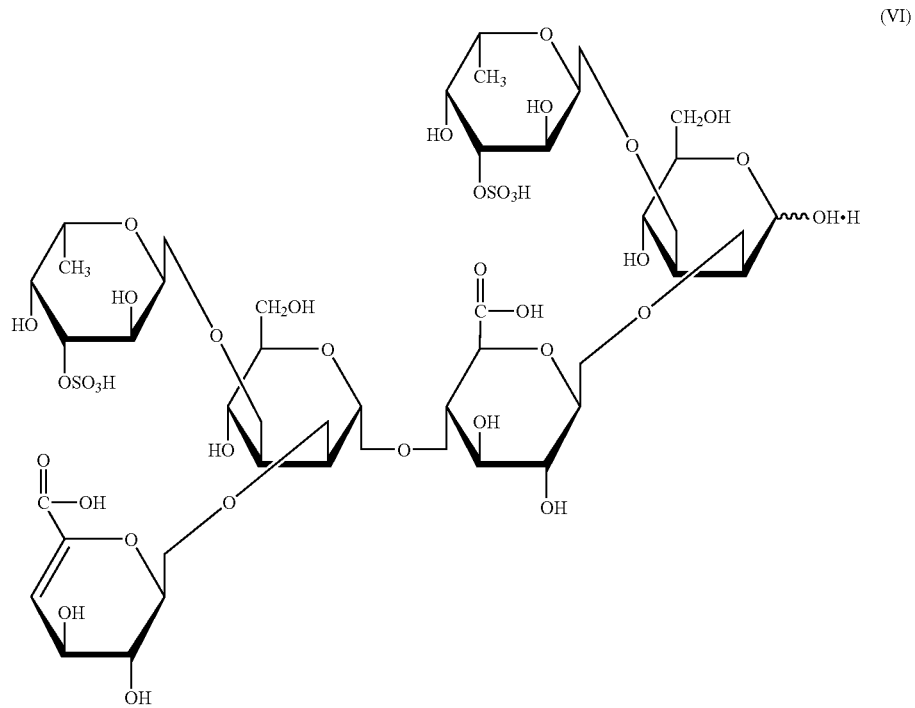

(VI)

PREPARATION EXAMPLE 6

(1) Two-hundred milligrams (1.1 mmol) of D-(+)-glucose was dissolved in 10 mL of pyridine, and 1.05 g (6.6 mmol) of Pyridine Sulfur Trioxide Complex (Pyr•SO₃: manufactured by Tokyo Kasei) was added thereto at room temperature. Thereafter, the resulting mixture was stirred at room temperature for several minutes and further stirred at 60° C. for 1 hour. The reaction solution was diluted with water and the pH of the solution was adjusted to near neutrality with an aqueous saturated barium hydroxide solution, and the resulting solution was then dried under reduced pressure. Water was again added to the resulting concentrate, and the resulting solution was again dried under reduced pressure. These steps were repeated one more time. A small amount of water was added to the resulting concentrate, and precipitates of barium sulfate were removed by centrifugation. The resulting supernatant was applied onto a cationic exchange column [Amberlite IRA-120 (Na⁺) (Organo)]. Finally, the resulting column-effluent fractions were concentrated under reduced pressure, to give 700 mg of sulfated D-(+)-glucose.

(2) Five-hundred grams (3.05 mmol) of L-fucose was dissolved in 10 mL of pyridine, and 2.33 g (14.6 mmol) of Pyr•SO₃ was added thereto at room temperature. Thereafter, the resulting mixture was stirred at room temperature for several minutes, and further stirred at 60° C. for 1 hour. The same procedures as in item (1) of Preparation Example 6 were carried out hereinbelow, to give sodium salt of sulfated fucose.

EXAMPLE 1

Method of Continuously Culturing CTLs Having Antizen-Specific Cytotoxic Activity

EXAMPLE 1-1

(1) Isolation and Storage of PBMCs

Blood was collected from a human normal individual donor having HLA-A24 or HLA-A2.1. The collected blood was diluted 2-folds with PBS(-), overlaid on Ficoll-paque (manufactured by Pharmacia), and centrifuged at 500×g for 20 minutes. The peripheral blood mononuclear cells (PBMCs) in the intermediate layer were collected with a pipette, and washed. The collected PBMCs were suspended in a storage solution of 90% FCS (manufactured by JRH Biosciences)/10% dimethyl sulfoxide (manufactured by SIGMA), and stored in liquid nitrogen. During CTL induction, these stored PBMCs were rapidly melted in water bath at 37° C., and washed with RPMI 1640 medium (manufactured by Bio Whittaker) containing 10 μg/ml Dnase (manufactured by Calbiochem). Thereafter, the number of living cells was calculated by trypan blue staining method, and subjected to each experiment.

(2) Induction of Anti-Influenza Virus Memory CTLs

The induction of anti-influenza virus memory CTLs was performed by partially modifying the method of Bednarek et al. (Bednarek, M. A. et al (1991 *J. Immunology*, 147, 4047-4053). Concretely, PBMCs prepared in item (1) of Example 1-1 were suspended in RPMI 1640 medium (manufactured by Bio Whittaker) containing 5% human AB-type serum, 0.1 mM nonessential amino acids, 1 mM sodium pyruvate, 2 mM L-glutamine (hereinabove being all manufactured by Bio Whittaker), 10 mM HEPES (manufactured by nakalai tesque), 1% streptomycin-penicillin (manufactured by Gibco BRL) (hereinafter simply referred to as "5HRPMI") so as to have a concentration of $4 \times 10^6$ cells/ml. Thereafter, the suspension was spread on a 24-well cell culture plate (manufactured by Falcon) in a volume of 1 ml/well, and the cells were incubated in a 5% $CO_2$ wet-type incubator at 37° C. for 1.5 hours, to give plastic-adherent monocytes. Thereafter, non-adherent cells were collected using RPMI medium, and stored on ice as responder cells. To separated monocytes was added 0.5 ml each of 5HRPMI containing as an antigen peptide 5 μg/ml epitope peptide derived from influenza virus protein [HLA A24-binding peptide (FluNPA24) RFYIQMC-TEL derived from the nucleoprotein of SEQ ID NO: 1 of Sequence Listing or HLA A2.1-binding peptide (FluMPA2.1) GILGFVFI™ derived from the matrix protein of SEQ ID NO: 2 of Sequence Listing] and 1 μg/ml β2 microglobulin (manufactured by Scripts). The mixture was incubated at room temperature for 2 hours, and thereafter the cells were subjected to X-ray irradiation (5500R) to give antigen-presenting cells. The peptide solution was removed by suction from each of the wells, and the wells were washed with RPMI 1640 medium. Thereafter, the responder cells previously stored on ice were suspended in 5HRPMI so as to have a concentration of 1 to $2 \times 10^6$ cells/ml, and the suspension was added to antigen-presenting cells in an amount of 1 ml per well. At this time, the sample was added so as to have a final concentration of 10 μg/ml. A group with no addition of the sample was used as the control. As the sample, the fucoidan derived from *Kjellmaniella crassifolia* prepared in Preparation Example 1 was used. The plate was cultured at 37° C. in the presence of 5% $CO_2$. On the second day from the initiation of the culture, 1 ml of 5 HRPMI containing 60 U/ml IL-2 (manufactured by Shionogi & Co., Ltd.) and the 10 μg/ml sample, the same sample as that initially added was added to each well (the control containing only IL-2). Also, on the fifth day, a half of the culture supernatant was removed, and 1 ml each of IL-2 and a sample-containing medium (the control containing only IL-2), the same as those mentioned above, were added thereto. On the seventh day the antigen-presenting cells were prepared in the same manner as above, and thereafter the responder cells which were cultured for one week were suspended in 5HRPMI so as to have a concentration of 1 to $2 \times 10^6$ cells/ml. The suspension was added to the antigen-presenting cells prepared in the same manner as above in an amount of 1 ml/well, and the cells were re-stimulated. At this time, the sample was added so as to have a final concentration of 10 μg/ml (the control being no addition). On the second day from re-stimulation, 1 ml of 5 HRPMI containing 60 U/ml IL-2 and the 10 μg/ml sample was added to each well (the control containing only IL-2). Also, on the fifth day, a half of the culture supernatant was removed, and 1 ml each of the medium having the same content as that before removal was added thereto (the control containing only IL-2). The culture was continued for additional two days, thereby inducing CTLs.

(3) Determination for Cytotoxic Activity of CTLs

The cytotoxic activity of CTLs on the fourteenth day after the initiation of induction prepared in item (2) of Example 1-1 was evaluated by a determination method for cytotoxic activity using Calcein-AM (Rudolf Lichtenfels et al., *J. Immunological Methods*, 172 (1994) 227-239).

HLA-A24 or A2.1-having EBV transformed B-cells (TISI or 221A2.1), which were cultured overnight together with an epitope peptide or in the absence of the epitope peptide, were suspended in RPMI 1640 medium containing 5% FCS (manufactured by JRH Biosciences) so as to have a concentration of $1 \times 10^6$ cells/ml. Thereafter, Calcein-AM (manufactured by Dojindo Corporate Headquarters) was added to the suspension so as to have a final concentration of 25 μM, and the cells were cultured at 37° C. for 1 hour. The cells were washed with a medium not containing Calcein-AM, and thereafter mixed with K562 cells in an amount 20 times that of the cells, to give Calcein-labeled target cells. The K562 cells were used for excluding nonspecific cytotoxic activity by NK cells admixed in the responder cells.

The memory CTLs prepared in item (2) of Example 1-1 were stepwise diluted with 5HRPMI so as to have a concentration of from $1 \times 10^5$ to $9 \times 10^6$ cells/ml as effector cells. Thereafter, each of the dilutions was poured into each well of 96-well cell culture plate in an amount of 100 μl/well each. Thereto were added the Calcein-labeled target cells prepared to have a concentration of $1 \times 10^5$ cells/ml in an amount of 100 μl/well. The plate containing the above-cell suspension was centrifuged at 400 g for 1 minute, and thereafter incubated in a wet-type $CO_2$ incubator at 37° C. for 4 hours.

After 4. hours, 100 μl of the culture supernatant was collected from each well, and the amount of calcein released into the culture supernatant was determined by using fluorescence plate reader (485 nm/538 nm). The specific cytotoxic activity was calculated by the following equation 1:

Specific Cytotoxic Activity (%)=[(Found Value in Each Well−Minimum Released Amount)/(Maximum Released Amount−Minimum Released Amount)]×100     [Equation 1]

In the above equation, the minimum released amount is the amount of calcein released in the well containing only target cells and K562 cells, showing the amount of calcein naturally released from the target cells. In addition, the maximum released amount refers to the amount of calcein released when the cells are completely disrupted by adding the surfactant Triton X-100 (manufactured by nakalai tesque) to the target cells. As a result, the specific cytotoxic activity was induced immediately after the induction, but there was no difference in the cytotoxic activity by the presence or absence of the addition of the sample during the induction.

(4) Continuous Culture of CTLs

CTLs prepared in item (2) of Example 1-1, which were confirmed to have epitope peptide-specific cytotoxic activity in item (3) of Example 1-1, were washed with 5HRPMI, and thereafter continuously cultured for additional 10 to 14 days in 5HRPMI containing 30 U/ml IL-2. During the continuous culture, a group with addition of the sample during the CTL induction was cultured by adding to the medium the same sample at the same concentration as that during the CTL induction. Also, the control with no addition of the sample during the CTL induction was continued culturing, without adding any sample. Stimulation by a peptide was not added at all during the continuous culture, and a half of the culture supernatant was removed every 2 to 3 days. Thereafter, a medium having the same composition as that before the removal of the culture supernatant was added thereto in an amount of 1 ml at a time. After continuous culture, the specific cytotoxic activity of CTLs was determined in the same manner as in item (3) of Example 1-1. The determination results are shown in Table 1. In the table, an E/T ratio means a ratio of the number of the effector cells (E) to the number of the target cells (T), and the peptide addition means the presence of peptide addition to the target cells.

TABLE 1

| Peptide | Sample | Addition of Sample | | | Cytotoxic Activity (%) | | |
|---------|--------|---------|---------|---------|---|---|---|
| | | During CTL Induction | During Culture with IL-2 | Peptide Addition | | | |
| | | | | | E/T Ratio | | |
| | | | | | 1 | 3 | 10 |
| FluMPA 2.1 | Control | − | − | − | N.T. | N.T. | 0 |
| | | − | − | − | N.T. | N.T. | 0 |
| | | | | | E/T Ratio | | |
| | | | | | 0.7 | 2.2 | 7 |
| | Fucoidan Derived from *Kjellmaniella crassifolia* | + | + | − | 0 | 0 | 0 |
| | | + | + | + | 22.9 | 52.7 | 80.6 |
| | | | | | E/T Ratio | | |
| | | | | | 1 | 3 | 10 |
| FluNPA 24 | Control | − | − | − | 0 | 0 | 11.8 |
| | | − | − | + | 5.7 | 21 | 65.1 |
| | Fucoidan Derived from *Kjellmaniella crassifolia* | + | + | − | 1.6 | 0 | 7.5 |
| | | + | + | + | 28.6 | 66.9 | 96.9 |

(N.T. means not tested.)

As a result, in the group with addition of the sample at both of the stage during the CTL induction and the stage during the continuous culture, its high activity was maintained even after continuous culture for 10 to 14 days. However, on the other hand, in the group with no addition of the fucoidan derived from *Kjellmaniella crassifolia* in both of the stage during the CIL induction and the stage during the continuous culture (control group), its activity was clearly lowered.

It was clarified from the above that the continuous culture of CTLs having an antigen-specific cytotoxic activity can be carried out without addition of the stimulus by peptide or the like during the continuous culture by adding the fucoidan derived from *Kjellmaniella crassifolia* during the CTL induction and during the continuous culture.

EXAMPLE 1-2

(1) Induction of Anti-Influenza Virus Memory CTLs

The induction of anti-influenza virus memory CTLs was carried out in the same manner as in item (2) of Example 1-1 using the PBMCs which were separated and stored in the same manner as in item (1) of Example 1-1. During the induction, the fucoidan derived from *Kjellmaniella crassifolia* prepared in Preparation Example 1, Fraction III (F-fucoidan) or Fraction II (U-fucoidan) prepared in Preparation Example 2, or 7-12SFd-F prepared in Preparation Example 3 was added to a medium as a sample so as to have a final concentration of 10 µg/ml. As the control, the group with no addition of the sample was used.

The cytotoxic activity of CTLs on the fourteenth day after the initiation of induction which were prepared as described above was evaluated in the same manner as in item (3) of Example 1-1. As a result, the antigen-specific cytotoxic activity was induced immediately after the induction, but there was no difference in the cytotoxic activity by the presence or absence of the addition of the sample during the induction and by the difference in the sample.

(2) Continuous Culture of CTLs

CTLs prepared in item (1) of Example 1-2 were continuously cultured for additional 10 to 14 days in the same manner as in item (4) of Example 1-1. During culture, as a sample, each sample which was added during the CTL induction in item (1) of Example 1-2 was added to a medium so as to have a final concentration of 10 µg/ml. The control with no addition of the sample during the CTL induction was continuously cultured without addition of the sample. After the continuous culture, the specific cytotoxic activity of CTLs was determined in the same manner as in item (3) of Example 1-1. The determination results are shown in Table 2.

TABLE 2

| Peptide | Sample | Addition of Sample | | | Cytotoxic Activity (%) E/T Ratio | | |
|---------|--------|---------|---------|---------|---|---|---|
| | | During CTL Induction | During Culture with IL-2 | Peptide Addition | 1 | 3 | 10 |
| FluMPA 2.1 | Control | − | − | − | 4.6 | 5.0 | 13.1 |
| | | − | − | + | 11.0 | 23.4 | 47.9 |
| | Fucoidan Derived from | + | + | − | 5.9 | 4.9 | 12.3 |
| | | + | + | + | 53.3 | 86.0 | 100.9 |

TABLE 2-continued

| Peptide | Sample | Addition of Sample During CTL Induction | During Culture with IL-2 | Peptide Addition | Cytotoxic Activity (%) E/T Ratio 1 | 3 | 10 |
|---|---|---|---|---|---|---|---|
| | *Kjellmaniella crassifolia* | | | | | | |
| | F-Fucoidan | + | + | − | 2.1 | 2.4 | 7.2 |
| | | + | + | + | 41.1 | 66.8 | 82.8 |
| | U-Fucoidan | + | + | − | 1.6 | 4.1 | 9.2 |
| | | + | + | + | 46.3 | 75.2 | 92.3 |
| | 7-12SFd-F | + | + | − | 0.3 | 2.2 | 11.7 |
| | | + | + | + | 12.0 | 37.9 | 60.7 |

As a result, in any of the groups with addition of the sample at both of the stage during the CTL induction and the stage during the continuous culture, their high activities were maintained even after continuous culture for 10 to 14 days. However, on the other hand, in the group with no addition of the sample in both of the stage during the CTL induction and the stage during the continuous culture (control), its activity was clearly lowered.

It was clarified from the above that the continuous culture of CTLs maintaining an antigen-specific cytotoxic activity can be carried out without addition of the stimulus by peptide or the like during the continuous culture by adding the fucoidan derived from *Kjellmaniella crassifolia*, F-fucoidan, U-fucoidan or 7-12SFd-F during the CTL induction and during the continuous culture.

EXAMPLE 1-3

(1) Induction of Anti-Influenza Virus Memory CTLs

The induction of anti-influenza virus memory CTLs was carried out in the same manner as in item (2) of Example 1-1 using the PBMCs which were separated and stored in the same manner as in item (1) of Example 1-1. During the induction, as a sample, L. M. W. heparin (trade name: Ardeparin sodium, manufactured by CELSUS LABORATORIES INC.), non-swellable alginic acid (manufactured by Wako Pure Chemical Industries, Ltd.), swellable alginic acid (manufactured by Wako Pure Chemical Industries, Ltd.), sodium salt of sulfated glucose prepared in item (1) of Preparation Example 6, or sodium chondroitin sulfate A (manufactured by Seikagaku Corporation) was added to a medium so as to have a final concentration of 10 μg/ml. As the control, the group with no addition of the sample was used. As an antigenic peptide, FluMPA2.1 was used.

The cytotoxic activity of CTLs on the fourteenth day after the initiation of induction which were prepared as described above was evaluated in the same manner as in item (3) of Example 1-1. As a result, the specific cytotoxic activity was induced immediately after the induction, but there was no difference in the cytotoxic activity by the presence or absence of the addition of the sample during the induction and by the difference in the sample.

(2) Continuous Culture of CTLs

CTLs prepared in item (1) of Example 1-3 were continuously cultured for additional 10 to 14 days in the same manner as in item (4) of Example 1-1. During the continuous culture, each of the samples which were the same as those added during the CTL induction in item (1) of Example 1-3 was added to a medium so as to have a final concentration of 10 μg/ml. The control with no addition of the sample during the CTL induction was continuously cultured without addition of the sample. After the continuous culture, the specific cytotoxic activity of CTLs was determined in the same manner as in item (3) of Example 1-1. The determination results are shown in Table 3.

TABLE 3

| Sample | Addition of Sample During CTL Induction | During Culture with IL-2 | Peptide Addition | Cytotoxic Activity (%) E/T Ratio 1 | 3 | 10 |
|---|---|---|---|---|---|---|
| Control | − | − | − | 17.4 | 26.5 | 35.2 |
| | − | − | + | 28.0 | 43.8 | 63.7 |
| L. M. W. Heparin | + | + | − | | 11.7 | 14.2 |
| | + | + | + | | 49.0 | 71.7 |
| Non-Swellable Alginic Acid | + | + | − | 12.9 | 24.8 | 14.0 |
| | + | + | + | 28.1 | 52.7 | 77.1 |
| Swellable Alginic Acid | + | + | − | 12.5 | 26.5 | 22.2 |
| | + | + | + | 39.8 | 75.3 | 86.9 |
| Sulfated Glucose | + | + | − | 14.3 | 27.8 | 21.0 |
| | + | + | + | 34.0 | 67.8 | 92.1 |
| Chondroitin Sulfate A | + | + | − | | | 21.1 |
| | + | + | + | | | 75.5 |

As a result, in any of the groups with addition of these samples at both of the stage during the CTL induction and the stage during the continuous culture, their high activities were maintained even after continuous culture. However, on the other hand, in the group with no addition of the sample in both of the stage during the CTL induction and the stage during the continuous culture (control), its activity was clearly lowered.

It was clarified from the above that, likewise as in the fucoidan, the continuous culture of CTLs having an antigen-specific cytotoxic activity can be carried out without addition of the stimulus by peptide or the like by adding heparin, which is a sulfated polysaccharide, or sodium chondroitin sulfate A during the CTL induction and during the continuous culture. In other words, it was clarified that similar activities can be found in sulfated polysaccharides other than the fucoidan. Furthermore, besides the sulfated polysaccharides, similar activities to those of the fucoidan were also found in sodium salt of sulfated glucose, which is a sulfated monosaccharide. Therefore, it was clarified that sulfated saccharides have effects for maintaining cytotoxic activity regardless of their sizes. On the other hand, similar activities to those of the fucoidan were found in non-swellable alginic acid and swellable alginic acid, which are not a sulfated saccharide. Therefore, the above-mentioned activities are not peculiar to the sulfated saccharides, but any saccharides can exhibit effects for maintaining cytotoxic activity as long as the saccharides are acidic saccharides, regardless of the kinds of the saccharides.

EXAMPLE 1-4

(1) Induction of Anti-Influenza Virus Memory CTLs

The induction of anti-influenza virus memory CTLs was carried out in the same manner as in item (2) of Example 1-1 using the PBMCs which were separated and stored in the same manner as in item (1) of Example 1-1. During the induction, as a sample, pectic acid (manufactured by nakalai tesque), sodium salt of sulfated fucose prepared in item (2) of Preparation Example 6, and sodium chondroitin sulfate B (manufactured by Seikagaku Corporation) was added to a medium so as to have a final concentration of 10 μg/ml, respectively. As the control, the group with no addition of the sample was used. As an antigenic peptide, FluMPA2.1 was used.

The cytotoxic activity of CTLs on the fourteenth day after the initiation of induction which were prepared as described above was evaluated in the same manner as in item (3) of Example 1-1. As a result, the specific cytotoxic activity was induced immediately after the induction, but there was no difference in the cytotoxic activity by the presence or absence of the addition of the sample during the induction and by the difference in the sample.

(2) Continuous Culture of CTLs

CTLs prepared in item (1) of Example 1-4 were continuously cultured for additional 10 to 14 days in the same manner as in item (4) of Example 1-1. During the continuous culture, the same sample as that added during the CTL induction in item (1) of Example 1-4 was added to a medium so as to have a final concentration of 10 μg/ml. The control with no addition of the sample during the CTL induction was continuously cultured without addition of the sample. After the continuous culture, the specific cytotoxic activity of CTLs was determined in the same manner as in item (3) of Example 1-1. The determination results are shown in Table 4.

TABLE 4

| Sample | Addition of Sample | | | Cytotoxic Activity (%) E/T Ratio | | |
|---|---|---|---|---|---|---|
| | During CTL Induction | During Culture with IL-2 | Peptide Addition | 2.5 | 5 | 10 |
| Control | − | − | − | 0.5 | 4.0 | N.T. |
| | − | − | + | 10.9 | 19.7 | N.T. |
| Pectic Acid | + | + | − | 3.4 | 5.5 | N.T. |
| | + | + | + | 32.0 | 49.4 | N.T. |
| Sulfated Fucose | + | + | − | 0 | 0 | 0.2 |
| | + | + | + | 17.6 | 36.6 | 55.3 |
| Chondroitin Sulfate B | + | + | − | 0 | 0 | 0.8 |
| | + | + | + | 28.1 | 38.1 | 60.7 |

(N.T. means not tested.)

As a result, in any of the groups with addition of these samples at both of the stage during the CTL induction and the stage during the continuous culture, their high activities were maintained even after continuous culture. However, on the other hand, in the group with no addition of the sample in both of the stage during the CTL induction and the stage during the continuous culture (control), its activity was clearly lowered.

It was clarified from the above that any of sodium chondroitin sulfate B, which is a sulfated polysaccharide, sodium salt of sulfated fucose, which is a sulfated monosaccharide, and pectic acid, which is an acidic polysaccharide have effects for maintaining cytotoxic activity.

EXAMPLE 1-5

(1) Induction of Anti-Influenza Virus Memory CTLs

The induction of anti-influenza virus memory CTLs was carried out in the same manner as in item (2) of Example 1-1 using the PBMCs which were separated and stored in the same manner as in item (1) of Example 1-1. During the induction, the samples as used in Examples described above were not used at all. As an antigenic peptide, FluMPA2.1 was used.

The cytotoxic activity of CTLs on the fourteenth day after the initiation of induction which were prepared as described above was evaluated in the same manner as in item (3) of Example 1-1.

(2) Continuous Culture of CTLs

CTLs prepared in item (1) of Example 1-5 were continuously cultured for additional 10 to 14 days in the same manner as in item (4) of Example 1-1. During the continuous culture, as a sample, the fucoidan derived from *Kjellmaniella crassifolia* prepared in Preparation Example 1, Fraction III (F-fucoidan) or Fraction II (U-fucoidan) prepared in Preparation Example 2, L. M. W. heparin (trade name: Ardeparin sodium, manufactured by CELSUS LABORATORIES INC.), pectic acid (manufactured by nakalai tesque), non-swellable alginic acid (manufactured by Wako Pure Chemical Industries, Ltd.), swellable alginic acid (manufactured by Wako Pure Chemical Industries, Ltd.), sodium salt of sulfated glucose prepared in item (1) of Preparation Example 6, sodium salt of sulfated fucose prepared in item (2) of Preparation Example 6, or sodium chondroitin sulfate B (manufactured by Seikagaku Corporation) was added to a medium so as to have a final concentration of 10 μg/ml, respectively. After the continuous culture, the specific cytotoxic activity of CTLs was determined in the same manner as in item (3) of Example 1-1. The determination results are shown in Tables 5 and 6.

TABLE 5

| Sample | Addition of Sample During CTL Induction | Addition of Sample During Culture with IL-2 | Peptide Addition | Cytotoxic Activity (%) E/T Ratio 1 | 3 | 10 |
|---|---|---|---|---|---|---|
| Control | − | − | − | 0 | 1.6 | 4.9 |
|  | − | − | + | 5.6 | 7.0 | 13.7 |
| Fucoidan Derived from Kjellmaniella crassifolia | − | + | − | 0 | 0 | 3.1 |
|  | − | + | + | 7.0 | 11.0 | 27.9 |
| F-Fucoidan | − | + | − | 0 | 0 | 1.6 |
|  | − | + | + | 7.4 | 20.4 |  |
| U-Fucoidan | − | + | − | 0 | 0 |  |
|  | − | + | + | 7.6 | 17.5 |  |
| L. M. W. Heparin | − | + | − | 0 |  |  |
|  | − | + | + | 18.3 |  |  |
| Pectic Acid | − | + | − | 0 |  |  |
|  | − | + | + | 16.5 |  |  |

TABLE 6

| Sample | Addition of Sample During CTL Induction | Addition of Sample During Culture with IL-2 | Peptide Addition | Cytotoxic Activity (%) E/T Ratio 1 | 3 | 10 |
|---|---|---|---|---|---|---|
| Control | − | − | − | 0 | 1.6 | 4.9 |
|  | − | − | + | 5.6 | 7.0 | 13.7 |
| Non-Swellable Alginic Acid | − | + | − | 3.9 | 4.6 | 6.1 |
|  | − | + | + | 9.5 | 13.8 | 24.9 |
| Swellable Alginic Acid | − | + | − | 3.3 | 1.3 | 8.8 |
|  | − | + | + | 12.6 | 18.7 | 35.6 |
| Sulfated Glucose | − | + | − | 2.2 | 2.4 | 7.5 |
|  | − | + | + | 8.1 | 17.8 | 32.5 |
| Sulfated Fucose | − | + | − | 0 | 0.4 | 3.3 |
|  | − | + | + | 8.9 | 12.6 | 26.4 |
| Chondroitin Sulfate B | − | + | − | N.T. | N.T. | 4.6 |
|  | − | + | + | N.T. | N.T. | 24.0 |

(N.T. means not tested.)

As a result, in any of the groups with addition of these samples during continuous culture, their high activities were maintained even after the continuous culture even when the samples were not added during the CTL induction. However, in the group with no addition of the sample in the stage during the continuous culture (control), its activity was clearly lowered.

It was clarified from the above that the continuous culture of CTLs maintaining an antigen-specific cytotoxic activity can be carried out without addition of the stimulus by peptide or the like by adding the fucoidan derived from *Kjellmaniella crassifolia*, F-fucoidan, U-fucoidan, the L. M. W. heparin, pectic acid (manufactured by nakalai tesque), the non-swellable alginic acid, the swellable alginic acid, the sodium salt of sulfated glucose, the sodium salt of sulfated fucose, or sodium chondroitin sulfate B during the continuous culture. In other words, it was clarified that the continuous culture of CTLs maintaining an antigen-specific cytotoxic activity can be carried out by adding an acidic saccharide only during the continuous culture.

EXAMPLE 1-6

(1) Induction of Anti-Influenza Virus Memory CTLs

The induction of anti-influenza virus memory CTLs was carried out in the same manner as in item (2) of Example 1-1 using the PBMCs which were separated and stored in the same manner as in item (1) of Example 1-1. During the induction, as a sample, the fucoidan derived from *Kjellmaniella crassifolia* prepared in Preparation Example 1, Fraction III (F-fucoidan) or Fraction II (U-fucoidan) prepared in Preparation Example 2 was added to a medium so as to have a final concentration of 10 μg/ml. As the control, the group with no addition of the sample was used. As an antigenic peptide, FluMPA2.1 was used.

The cytotoxic activity of CTLs on the fourteenth day after the initiation of induction which were prepared as described above was evaluated in the same manner as in item (3) of Example 1-1. As a result, the specific cytotoxic activity was induced immediately after the induction, but there was no difference in the cytotoxic activity by the presence or absence of the addition of the sample during the induction and by the difference in the sample.

(2) Continuous Culture of CTLs

CTLs prepared in item (1) of Example 1-6 were continuously cultured for additional 10 to 14 days in the same manner as in item (4) of Example 1-1. During the continuous culture, there were used the group with addition of the same samples as those added during the CTL induction in item (1) of Example 1-6 so as to have a final concentration of 10 μg/ml, respectively, and the group with no addition of the sample. The control with no addition of the sample during the CTL induction was continuously cultured without addition of the sample. After the continuous culture, the specific cytotoxic activity of CTLs was determined in the same manner as in item (3) of Example 1-1. The determination results are shown in Table 7.

TABLE 7

| Sample | Addition of Sample During CTL Induction | Addition of Sample During Culture with IL-2 | Peptide Addition | Cytotoxic Activity (%) E/T Ratio 2 | 10 | 30 |
|---|---|---|---|---|---|---|
| Control | − | − | − | 4.6 | 5.0 | 13.1 |
|  | − | − | + | 11.0 | 23.4 | 47.9 |
| Fucoidan Derived from Kjellmaniella crassifolia | + | + | − | 5.9 | 4.9 | 12.3 |
|  | + | + | + | 53.3 | 86.0 | 100.9 |
|  | + | − | − | 0 | 0 | 4.5 |
|  | + | − | + | 46.0 | 78.5 | 98.7 |
| F-Fucoidan | + | + | − | 2.1 | 2.4 | 7.2 |
|  | + | + | + | 41.5 | 66.8 | 82.8 |
|  | + | − | − | 0 | 0 | 3.2 |
|  | + | − | + | 37.6 | 63.5 | 86.3 |
| U-Fucoidan | + | + | − | 1.6 | 4.1 | 9.2 |
|  | + | + | + | 46.3 | 75.2 | 92.3 |
|  | + | − | − | 0 | 0 | 4.5 |
|  | + | − | + | 43.5 | 71.9 | 91.1 |

As a result, in the groups with addition of these samples during the CTL induction, their high activities were maintained even after the continuous culture regardless of whether or not the sample was added during the continuous culture. However, on the other hand, in the group with no addition of the sample (the fucoidan derived from *Kjellmaniella crassifolia*) in both of the stage during the CTL induction and the stage during the continuous culture (control), its activity was clearly lowered.

It was clarified from the above that the continuous culture of CTLs having an antigen-specific cytotoxic activity can be carried out without addition of the stimulus by peptide or the like during the continuous culture even when an acidic saccharide such as the fucoidan derived from *Kjellmaniella crassifolia* was added during the CTL induction but not during the continuous culture.

It was clarified from the above results that the continuous culture of CTLs maintaining an antigen-specific cytotoxic activity of CTLs for a long period of time can be carried out by adding an acidic saccharide during the CTL induction and the continuous culture. Furthermore, it was clarified that the continuous culture of CTLs with maintaining an antigen-specific cytotoxic activity of CTLs for a long period of time can be carried out even when an acidic saccharide was added at only one of the stage during the CIL induction or the stage during the continuous culture.

EXAMPLE 2

Expansion of CTLs Having Antigen-Specific Cytotoxic Activity

EXAMPLE 2-1

(1) Induction of Anti-Influenza Virus Memory CTLs

The induction of anti-influenza virus memory CTLs was carried out in the same manner as in item (2) of Example 1-1 using the PBMCs which were separated and stored in the same manner as in item (1) of Example 1-1. During the induction, as a sample, the fucoidan derived from Kjellmaniella crassifolia prepared in Preparation Example 1 was added to a medium so as to have a final concentration of 10 μg/ml. Further, a group with no addition of the sample was used.

The cytotoxic activity of CTLs on the fourteenth day after the initiation of induction which were prepared as described above was evaluated in the same manner as in item (3) of Example 1-1. As a result, the specific cytotoxic activity had been induced immediately after the induction, but there was no difference in the cytotoxic activity by the presence or absence of the addition of the sample during the induction.

(2) Expansion of CTLs

CTLs prepared in item (1) of Example 2-1 were washed with 5HRPMI, and then made into a suspension having a concentration of $5 \times 10^4$ cells/ml. On the other hand, allogenic PBMCs not having HLA-A24 and HLA-A2.1 which were collected in the same manner as in item (1) of Example 1-1 were subjected to X-ray irradiation (3300R), and the cells were washed with the medium and then made into a suspension having a concentration of $5 \times 10^6$ cells/ml. These CTLs ($2.5 \times 10^4$ cells) and allogenic PBMCs ($1.25 \times 10^7$ cells) were suspended in 10 ml of 5HRPMI, and anti-CD3 antibody (manufactured by Janssen-Kyowa) was further added thereto so as to give a final concentration of 50 ng/ml. The mixture was placed into a flask of 12.5 cm$^2$ (manufactured by Falcon), and the cells were cultured in a wet-type $CO_2$ incubator at 37° C. for 14 days. During the culture, a group with addition of the fucoidan derived from Kjellmaniella crassifolia as a sample so as to have a final concentration of 10 μg/ml and a group with no addition of the sample were used. Stimulation by a peptide was not added at all during this culture. On the first day after the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 to each flask were carried out every 2 to 3 days. On this occasion, the fucoidan derived from Kjellmaniella crassifolia having the same concentration was added to the medium for the group with the sample addition. On the fourteenth day after the initiation of the expansion, the specific cytotoxic activity of CTLs was determined in the same manner as in item (3) of Example 1-1. The determination results are shown in Table 8. The expansion ratio (× times ratio) was calculated by dividing the cell count after the expansion by the cell count before the expansion.

TABLE 8

| | | Addition of Sample | | | | Cytotoxic Activity (%) E/T Ratio | | | |
|---|---|---|---|---|---|---|---|---|---|
| Peptide | Sample | During CTL Induction | During Expansion | Expansion Ratio | Peptide Addition | 1 | 3 | 10 | 30 |
| FluMPA2.1 | Control | − | − | × 494 | − | 2.5 | 1.2 | 2.0 | 8.4 |
| | | − | − | × 494 | + | 5.2 | 14.7 | 38.8 | 70.3 |
| | Fucoidan Derived from Kjellmaniella crassifolia | + | + | × 513 | − | 1.6 | 3.2 | 5.4 | 7.8 |
| | | + | + | × 513 | + | 22.2 | 47.4 | 87.0 | 108.3 |
| | | + | − | × 694 | − | 2.5 | 3.2 | 7.2 | 18.5 |
| | | + | − | × 694 | + | 21.0 | 44.7 | 84.2 | 102.8 |
| | | − | + | × 488 | − | 2.1 | 2.2 | 5.8 | 7.8 |
| | | − | + | × 488 | + | 10.5 | 26.4 | 62.3 | 83.8 |
| FluNPA24 | Control | − | − | × 316 | − | 13.0 | 7.3 | N.T. | |
| | | − | − | × 316 | + | 22.7 | 50.8 | N.T. | |
| | Fucoidan Derived from Kjellmaniella crassifolia | + | + | × 360 | − | 0 | 0 | N.T. | |
| | | + | + | × 360 | + | 35.7 | 76.7 | N.T. | |
| | | + | − | × 338 | − | 4.8 | 9.4 | N.T. | |
| | | + | − | × 338 | + | 48.6 | 85.1 | N.T. | |
| | | − | + | × 448 | − | 2.9 | 0 | N.T. | |
| | | − | + | × 448 | + | 26.7 | 76.2 | N.T. | |

(N.T. means not tested.)

As a result, in the groups with addition of the fucoidan derived from *Kjellmaniella crassifolia* in both of the stage during the CTL induction and the stage during the expansion, CTLs had specific, high cytotoxic activities even after the expansion for 14 days. On the other hand, in the group with no addition of the fucoidan derived from *Kjellmaniella crassifolia* in both of the stage during the CTL induction and the stage during the expansion, its activity was clearly lowered. In addition, in the group with the addition of the fucoidan derived from *Kjellmaniella crassifolia* during the expansion with an anti-CD3 antibody without the addition of the fucoidan derived from Kjellmaniella crassifolia during the CTL induction, and the group with the addition of the fucoidan derived from *Kjellmaniella crassifolia* during the CTL induction without the addition of the fucoidan during the expansion, the expansion of CTLs with maintaining a specific, high cytotoxic activity of CTLs can be carried out for a long period of time. In other words, it was clarified that the expansion of CTLs with maintaining a specific, high cytotoxic activity of CTLs can be carried out for a long period of time by adding the fucoidan derived from Kjellmaniella crassifolia in at least one of the stage during the CTL induction and the stage during the expansion.

EXAMPLE 2-2

(1) Induction of Anti-Influenza Virus Memory CTLS

The induction of anti-influenza virus memory CTLs was carried out in the same manner as in item (2) of Example 1-1 using the PBMCs which were separated and stored in the same manner as in item (1) of Example 1-1. During the induction, as a sample, the fucoidan derived from *Kjellmaniella crassifolia* prepared in Preparation Example 1, or Fraction III (F-fucoidan) or Fraction II (U-fucoidan) prepared in Preparation Example 2 was added to a medium so as to have a final concentration of 10 µg/ml, respectively. Further, the group with no addition of the sample was used. As an antigenic peptide, FluMPA2.1 was used.

The cytotoxic activity of CTLs on the fourteenth day after the initiation of induction which were prepared as described above was evaluated in the same manner as in item (3) of Example 1-1. As a result, the antigen-specific cytotoxic activity was induced immediately after the induction, but there was no difference in the cytotoxic activity by the presence or absence of the addition of the sample during the induction and by the difference in the sample.

(2) Expansion of CTLs

CTLs prepared in item (1) of Example 2-2 were expanded in the same manner as in item (2) of Example 2-1. During the expansion, there were used the group with the addition of the same samples as those added during the CTL induction in item (1) of Example 2-2 so as to have a final concentration of 10 µg/ml, respectively, and the group with addition of no sample at all from the stage of induction. Stimulation by a peptide was not added at all during the culture. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 to each flask were carried out every 2 to 3 days. However, in the group with no addition of the sample, the sample was not added even during medium exchange. On the fourteenth day after the initiation of the expansion, the specific cytotoxic activity of CTLs was determined in the same manner as in item (3) of Example 1-1. The determination results are shown in Table 9.

TABLE 9

| | Addition of Sample | | | | Cytotoxic Activity |
|---|---|---|---|---|---|
| Sample | During CTL Induction | During Culture with IL-2 | Expansion Ratio | Peptide Addition | (%) E/T Ratio 10 |
| Control | − | − | × 332 | − | 3.1 |
| | − | − | × 332 | + | 59.7 |
| Fucoidan Derived from *Kjellmaniella crassifolia* | + | + | × 388 | − | 2.4 |
| | + | + | × 388 | + | 85.2 |
| F-Fucoidan | + | + | × 340 | − | 2.1 |
| | + | + | × 340 | + | 77.7 |
| U-Fucoidan | + | + | × 290 | − | 1.2 |
| | + | + | × 290 | + | 81.6 |

As a result, in the group with addition of these samples during the CTL induction and during the expansion, CTLs maintained specific, high cytotoxic activity even after the expansion for 14 days. On the other hand, in the group with no addition of these samples in either of the stage during the CTL induction or the stage during the expansion, its activity was clearly lowered. In other 10 words, it was clarified that the expansion of CTLs can be carried out with maintaining the specific high cytotoxic activity for a long period of time by adding the fucoidan during the CTL induction and during the expansion, irrespective of the structures and the kinds of the fucoidan.

EXAMPLE 2-3

(1) Induction of Anti-Influenza Virus Memory CTLs

The induction of anti-influenza virus memory CTLs was carried out in the same manner as in item (2) of Example 1-1 using the PBMCs which were separated and stored in the same manner as in item (1) of Example 1-1. During the induction, as a sample, 7-12SFd-F prepared in Preparation Example 3 was added to a medium so as to have a final concentration of 10 µg/ml. Further, the group with no addition of the sample was used. As an antigenic peptide, FluMPA2.1 was used.

The cytotoxic activity of CTLs on the fourteenth day after the initiation of induction which were prepared as described above was evaluated in the same manner as in item (3) of Example 1-1. As a result, the antigen-specific cytotoxic activity was induced immediately after the induction, but there was no difference in the cytotoxic activity by the presence or absence of the addition of the sample during the induction.

(2) Expansion of CTLs

CTLs prepared in item (1) of Example 2-3 were expanded in the same manner as in item (2) of Example 2-1. During the expansion, there were used the group with the addition of the same samples as those added during the CTL induction in item (1) of Example 2-3 so as to have a final concentration of 10 µg/ml and the group with addition of no sample at all from the stage of induction. Stimulation by a peptide was not added at all during the culture. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 and 10 µg/ml 7-12FSd-F to each flask were carried out every 2 to 3 days. However, in the group with no addition of the sample, the sample was not added even during medium exchange. On the fourteenth day after the initiation of the expansion, the specific cytotoxic activity of CTLs was determined in the same manner as in item (3) of Example 1-1. The determination results are shown in Table 10.

TABLE 10

| Sample | Addition of Sample | | Expansion Ratio | Peptide Addition | Cytotoxic Activity (%) E/T Ratio | |
|---|---|---|---|---|---|---|
| | During CTL Induction | During Expansion | | | 3 | 10 |
| Control | − | − | × 260 | − | 2.5 | 5.0 |
| | − | − | × 260 | + | 54.2 | 84.3 |
| 7-12SFd-F | + | + | × 178 | − | 2.8 | 0 |
| | + | + | × 178 | + | 67.0 | 93.7 |

As a result, in the group with addition of 7-12SFd-F during the CIL induction and during the expansion, CTLs maintained specific, high cytotoxic activity even after the expansion for 14 days. On the other hand, in the group with no addition of the sample in either of the stage during the CTL induction or the stage during the expansion, its activity was clearly lowered. In other words, it was clarified that the expansion of CTLs can be carried out with maintaining the specific high cytotoxic activity for a long period of time by adding not only a polymeric sulfated polysaccharide such as fucoidan but also a sulfated saccharide having a low molecular weight, such as 7-12FSd-F, during the CTL induction and during the expansion.

EXAMPLE 2-4

(1) Induction of Anti-Influenza Virus Memory CTLs

The induction of anti-influenza virus memory CTLs was carried out in the same manner as in item (2) of Example 1-1 using the PBMCs which were separated and stored in the same manner as in item (1) of Example 1-1. During the induction, as a sample, each of L. M. W. heparin (trade name: Ardeparin sodium, manufactured by CELSUS LABORATORIES INC.), pectic acid (manufactured by nakalai tesque), a non-swellable alginic acid (manufactured by Wako Pure Chemical Industries, Ltd.), a swellable alginic acid (manufactured by Wako Pure Chemical Industries, Ltd.), sodium salt of sulfated glucose prepared in item (1) of Preparation Example 6, sodium salt of sulfated fucose prepared in item (2) of Preparation Example 6, sodium chondroitin sulfate A (manufactured by Seikagaku Corporation) or sodium chondroitin sulfate B (manufactured by Seikagaku Corporation) was added to a medium so as to have a final concentration of 10 µg/ml. Furthermore, the group with no addition of the sample was used. As an antigenic peptide, FluMPA2.1 was used.

The cytotoxic activity of CTLs on the fourteenth day after the initiation of induction which were prepared as described above was evaluated in the same manner as in item (3) of Example 1-1. As a result, the specific cytotoxic activity was induced immediately after the induction, but there was no difference in the cytotoxic activity by the presence or absence of the addition of the sample during the induction and by the difference in the sample.

(2) Expansion of CTLs

CTLs prepared in item (1) of Example 2-4 were expanded for additional 10 to 14 days in the same manner as in item (2) of Example 2-1. During the expansion, there were used the group with addition of the same samples as those added during the CTL induction in item (1) of Example 2-1 to a medium so as to have a final concentration of 10 µg/ml, respectively, and the group with no addition of the sample during the CTL induction at all from the stage of induction. Stimulation by a peptide was not added at all during the culture. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 and a 10 µg/ml sample to each flask were carried out every 2 to 3 days. However, in the group with no addition of the sample, the sample was not added even during medium exchange. On the fourteenth day after the initiation of the expansion, the specific cytotoxic activity of CTLs was determined in the same manner as in item (3) of Example 1-1. The determination results are shown in Table 11.

TABLE 11

| Sample | Addition of Sample | | Expansion Ratio | Peptide Addition | Cytotoxic Activity (%) E/T Ratio | |
|---|---|---|---|---|---|---|
| | During CTL Induction | During Expansion | | | 3 | 10 |
| Control | − | − | × 274 | − | 17.0 | 32.2 |
| | − | − | × 274 | + | 44.2 | 66.0 |
| L. M. W. Heparin | + | + | × 240 | − | 5.2 | 19.6 |
| | + | + | × 240 | + | 56.4 | 92.9 |
| Pectic Acid | + | + | × 160 | − | 11.6 | 7.3 |
| | + | + | × 160 | + | 47.0 | 69.8 |
| Non-Swellable Alginic Acid | + | + | × 220 | − | 26.2 | 26.8 |
| | + | + | × 220 | + | 63.5 | 81.4 |
| Swellable Alginic Acid | + | + | × 176 | − | 14.3 | 21.3 |
| | + | + | × 176 | + | 65.0 | 101.6 |
| Sulfated Glucose | + | + | × 220 | − | 10.3 | 25.6 |
| | + | + | × 220 | + | 62.3 | 127.4 |
| Sulfated Fucose | + | + | × 240 | − | | 23.3 |
| | + | + | × 240 | + | | 70.2 |
| Chondroitin Sulfate A | + | + | × 280 | − | 0 | 5.3 |
| | + | + | × 280 | + | 56.7 | 89.0 |
| Chondroitin Sulfate B | + | + | × 178 | − | 1.0 | 10.7 |
| | + | + | × 178 | + | 57.8 | 98.2 |

As a result, in the group with addition of these samples during the CTL induction and during the expansion, CTLs maintained specific, high cytotoxic activity even after the expansion for 14 days. On the other hand, in the group with no addition of the samples in either of the stage during the CTL induction or the stage during the expansion, its activity was clearly lowered. In other words, it was clarified that the expansion of CTLs can be carried out with maintaining the specific high cytotoxic activity for a long period of time by adding not only a sulfated saccharide but also an acidic saccharide, irrespective of the kinds, modifications and the like of the saccharide, during the CTL induction and during the expansion.

EXAMPLE 2-5

(1) Induction of Anti-Influenza Virus Memory CTLs

The induction of anti-influenza virus memory CTLs was carried out in the same manner as in item (2) of Example 1-1 using the PBMCs which were separated and stored in the same manner as in item (1) of Example 1-1. During the induction, the samples as used in Examples described above were not used at all. As an antigenic peptide, FluMPA2.1 was used.

The cytotoxic activity of CTLs on the fourteenth day after the initiation of induction which were prepared as described above was evaluated in the same manner as in item (3) of Example 1-1.

(2) Expansion of CTLs

CTLs prepared in item (1) of Example 2-5 were expanded for additional 10 to 14 days in the same manner as in item (2) of Example 2-1. During the expansion, there were used the group with addition of the sample so as to have a final concentration of 10 μg/ml, and the group with no addition of the sample. Stimulation by a peptide was not added at all during the culture. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 and a 10 μg/ml sample to each flask were carried out every 2 to 3 days. However, in the group with no addition of the sample, the sample was not added even during medium exchange. As the sample, Fraction III (F-fucoidan) prepared in Preparation Example 2 was used. On the fourteenth day after the initiation of the expansion, the specific cytotoxic activity of CTLs was determined in the same manner as in item (3) of Example 1-1. The determination results are shown in Table 12.

EXAMPLE 2-6

(1) Induction of Anti-Influenza Virus Memory CTLs

The induction of anti-influenza virus memory CTLs was carried out in the same manner as in item (2) of Example 1-1 using the PBMCs which were separated and stored in the same manner as in item (1) of Example 1-1. During the induction, the samples as used in Examples described above were not used at all. As an antigenic peptide, FluMPA2.1 was used.

The cytotoxic activity of CTLs on the fourteenth day after the initiation of induction which were prepared as described above was evaluated in the same manner as in item (3) of Example 1-1.

(2) Expansion of CTLs

CTLs prepared in item (1) of Example 2-6 were expanded for additional 10 to 14 days in the same manner as in item (2) of Example 2-1. During the expansion, there were used the group with addition of the sample to a medium so as to have a final concentration of 10 μg/ml, respectively, and the group with no addition of the sample. Stimulation by a peptide was not added at all during the culture. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 and a 10 μg/ml sample to each flask were carried out every 2 to 3 days. However, in the group with no addition of the sample, the sample was not added even during medium exchange. As the sample, the fucoidan derived from *Kjellmaniella crassifolia* prepared in Preparation Example 1, Fraction II (U-fucoidan) prepared in Preparation Example 2, 7-12SFd-F prepared in Preparation Example 3, L. M. W. heparin (trade name: Ardeparin sodium, manufactured by CELSUS LABORATORIES INC.), pectic acid (manufactured by nakalai tesque), a non-swellable alginic acid (manufactured by Wako Pure Chemical Industries,

TABLE 12

| | Addition of Sample | | | | Cytotoxic Activity (%) E/T Ratio | | | |
|---|---|---|---|---|---|---|---|---|
| Sample | During CTL Induction | During Expansion | Expansion Ratio | Peptide Addition | 1 | 3 | 10 | 30 |
| Control | − | − | × 393 | − | 1.5 | 1.0 | 3.1 | 5.9 |
| | − | − | × 393 | + | 3.8 | 15.7 | 36.7 | 60.2 |
| F-Fucoidan | − | + | × 475 | − | | | 0 | 1.7 |
| | − | + | × 475 | + | | | 40.7 | 76.3 |

As a result, in the group with addition of F-fucoidan during the expansion, CTLs maintained specific, high cytotoxic activity even after the expansion for 14 days. On the other hand, in the group with no addition of the sample in either of the stage during the CTL induction or the stage during the expansion, its activity was clearly lowered. In other words, it was clarified that the expansion of CTLs can be carried out with maintaining the specific high cytotoxic activity for a long period of time even when the F-fucoidan was not added during the induction but added only during the expansion.

Ltd.), a swellable alginic acid (manufactured by Wako Pure Chemical Industries, Ltd.), sodium salt of sulfated glucose prepared in item (1) of Preparation Example 6, sodium salt of sulfated fucose prepared in item (2) of Preparation Example 6, sodium chondroitin sulfate A (manufactured by Seikagaku Corporation) or sodium chondroitin sulfate B (manufactured by Seikagaku Corporation) was used. On the fourteenth day after the initiation of the expansion, the specific cytotoxic activity of CTLs was determined in the same manner as in item (3) of Example 1-1. The determination results are shown in Tables 13 and 14.

TABLE 13

| Sample | Addition of Sample During CTL Induction | During Expansion | Expansion Ratio | Peptide Addition | Cytotoxic Activity (%) E/T Ratio 1 | 3 | 10 | 30 |
|---|---|---|---|---|---|---|---|---|
| Control | − | − | × 403 | − | 0.8 | 1.9 | 4.5 | 9.9 |
|  | − | − | × 403 | + | 6.5 | 16.0 | 31.9 | 53.2 |
| Fucoidan Derived from | − | + | × 425 | − | 0 | 0 | 3.9 | 12.3 |
| *Kjellmaniella crassifolia* | − | + | × 425 | + | 13.1 | 18.3 | 40.3 | 72.4 |
| U-Fucoidan | − | + | × 358 | − | 0 | 0 | 2.9 | 5.3 |
|  | − | + | × 358 | + | 13.2 | 25.9 | 45.6 | 69.4 |
| 7-12SFd-F | − | + | × 310 | − | 2.7 | 0 | 1.0 | 3.5 |
|  | − | + | × 310 | + | 14.1 | 20.1 | 41.7 | 64.6 |
| L. M. W. Heparin | − | + | × 353 | − | 1.4 | 0 | 0.6 | 2.5 |
|  | − | + | × 353 | + | 11.3 | 22.2 | 43.9 | 71.2 |
| Pectic Acid | − | + | × 350 | − | 2.3 | 4.1 | 8.2 | 15.9 |
|  | − | + | × 350 | + | 18.2 | 33.3 | 64.2 | 87.8 |

TABLE 14

| Sample | Addition of Sample During CTL Induction | During Expansion | Expansion Ratio | Peptide Addition | Cytotoxic Activity (%) E/T Ratio 1 | 3 | 10 | 30 |
|---|---|---|---|---|---|---|---|---|
| Control | − | − | × 403 | − | 0.8 | 1.9 | 4.5 | 9.9 |
|  | − | − | × 403 | + | 6.5 | 16.0 | 31.9 | 53.2 |
| Non-Swellable Alginic Acid | − | + | × 335 | − | 0.5 | 5.2 | 6.5 | 14.4 |
|  | − | + | × 335 | + | 13.5 | 24.1 | 50.4 | 76.0 |
| Swellable Alginic Acid | − | + | × 378 | − | 0.1 | 0 | 2.1 | 10.6 |
|  | − | + | × 378 | + | 15.4 | 22.0 | 47.8 | 81.7 |
| Sulfated Glucose | − | + | × 343 | − | 2.8 | 0 | 0 | 3.6 |
|  | − | + | × 343 | + | 11.0 | 18.0 | 39.5 | 59.0 |
| Sulfated Fucose | − | + | × 448 | − |  |  | 0 | 1.3 |
|  | − | + | × 448 | + |  |  | 32.5 | 64.9 |
| Chondroitin Sulfate A | − | + | × 383 | − | 6.3 | 5.6 | 7.5 | 18.8 |
|  | − | + | × 383 | + | 8.0 | 18.7 | 36.6 | 67.6 |
| Chondroitin Sulfate B | − | + | × 383 | − | 3.9 | 4.4 | 8.3 | 11.8 |
|  | − | + | × 383 | + | 15.2 | 27.2 | 48.1 | 76.2 |

As a result, in the group with addition of these samples during the expansion, any of CTLs maintained specific, high cytotoxic activity even after the expansion for 14 days. On the other hand, in the group with no addition of the sample in either of the stage during the CTL induction or the stage during the expansion, its activity was clearly lowered. In other words, it was clarified that the expansion of CTLs can be carried out with maintaining the specific high cytotoxic activity for a long period of time even when the acidic saccharide was not added during the induction but added only during the expansion.

EXAMPLE 2-7

(1) Induction of Anti-Influenza Virus Memory CTLs

The induction of anti-influenza virus memory CTLs was carried out in the same manner as in item (2) of Example 1-1 using the PBMCs which were separated and stored in the same manner as in item (1) of Example 1-1. During the induction, a sample was added so as to have a final concentration of 10 μg/ml. Further, the group with no addition of sample was used. As the sample, the fucoidan derived from *Kjellmaniella crassifolia* prepared in Preparation Example 1, Fraction III (F-fucoidan) or Fraction II (U-fucoidan) prepared in Preparation Example 2, 7-12SFd-F prepared in Preparation Example 3, or L. M. W. heparin (trade name: Ardeparin sodium, manufactured by CELSUS LABORATORIES INC.) was used. As an antigenic peptide, FluMPA2.1 was used.

The cytotoxic activity of CTLs on the fourteenth day after the initiation of induction which were prepared as described above was evaluated in the same manner as in item (3) of Example 1-1. As a result, the specific cytotoxic activity was induced immediately after the induction, but there was no difference in the cytotoxic activity by the presence or absence of the addition of the sample during the induction and by the difference in the sample.

(2) Expansion of CTLs

CTLs prepared in item (1) of Example 2-7 were expanded in the same manner as in item (2) of Example 2-1. During the expansion, there were used the group with addition of the same samples as those added during the CTL induction in item (1) of Example 2-7 and the group with no addition of the sample, and the control group with no addition of the samples at all from the stage during the induction. Stimulation by a peptide was not added at all during the culture. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 and a 10 μg/ml sample to each flask were carried out every 2 to 3 days. However, in the group with no addition of the sample, the sample was not added even during medium exchange. On the fourteenth day after the initiation of the expansion, the specific cytotoxic activity of CTLs was determined in the same manner as in item (3) of Example 1-1. The determination results are shown in Table 15.

induction, as a sample, the fucoidan derived from *Kjellmaniella crassifolia* prepared in Preparation Example 1 was added so as to have a final concentration of 10 μg/ml. Further, the group with no addition of sample was used. As an antigenic peptide, FluMPA2.1 was used.

TABLE 15

| Sample | Addition of Sample During CTL Induction | During Expansion | Expansion Ratio | Peptide Addition | Cytotoxic Activity (%) E/T Ratio 1 | 3 | 10 | 30 |
|---|---|---|---|---|---|---|---|---|
| Control | − | − | × 393 | − | 1.5 | 1.0 | 3.1 | 5.9 |
|  | − | − | × 393 | + | 3.6 | 15.7 | 36.7 | 60.2 |
| Fucoidan Derived from | + | + | × 310 | − | 2.5 | 3.8 | 0 | 2.0 |
| *Kjellmaniella crassifolia* | + | + | × 310 | + | 15.1 | 30.9 | 76.7 | 77.9 |
|  | + | − | × 166 | − | 5.6 | 2.4 | 5.9 | 12.2 |
|  | + | − | × 166 | + | 15.3 | 30.2 | 65.2 | 88.3 |
| F-Fucoidan | + | + | × 278 | − | 1.5 | 1.2 | 4.4 | 1.3 |
|  | + | + | × 310 | + | 9.2 | 21.2 | 41.9 | 65.4 |
|  | + | − | × 175 | − | 2.2 | 0.8 | 1.2 | 2.4 |
|  | + | − | × 175 | + | 6.7 | 16.3 | 47.3 | 74.4 |
| U-Fucoidan | + | + | × 214 | − |  |  |  | 3.4 |
|  | + | + | × 214 | + |  |  |  | 66.7 |
|  | + | − | × 173 | − | 7.1 | 8.9 | 8.8 | 11.5 |
|  | + | − | × 173 | + | 10.6 | 23.2 | 46.0 | 77.0 |
| 7-12SFd-F | + | + | × 258 | − | 0 | 0 | 0 | 1.6 |
|  | + | + | × 258 | + | 9.4 | 23.4 | 44.2 | 82.1 |
|  | + | − | × 283 | − | 6.7 | 6.5 | 9.3 | 9.8 |
|  | + | − | × 283 | + | 14.0 | 34.6 | 50.4 | 83.5 |
| L. M. W. Heparin | + | + | × 243 | − | 5.6 | 2.5 | 1.1 | 0.9 |
|  | + | + | × 243 | + | 16.3 | 22.7 | 43.9 | 72.8 |
|  | + | − | × 253 | − | 5.2 | 4.5 | 6.6 | 7.0 |
|  | + | − | × 253 | + | 12.5 | 26.9 | 57.8 | 83.7 |

As a result, in any of the groups with addition of these samples in both of the stage during the CTL induction and the stage during the expansion and the groups with addition of these samples only during the CTL induction, CTLs after expansion for 14 days maintained specific, high cytotoxic activities. However, on the other hand, in the group with no addition of these samples in both of the stage during the CTL induction and the stage during the expansion, its activity was clearly lowered. In other words, it was clarified that the expansion of CTLs can be carried out with maintaining the specific high cytotoxic activity for a long period of time by adding the acidic saccharide during the induction, regardless of whether or not the acidic saccharide was added during the expansion.

It was clarified from the above results that the expansion of CTLs can be carried out maintaining the specific high cytotoxic activity for a long period of time by adding the acidic saccharide in one or both of the stage during the CTL induction and the stage during the expansion.

EXAMPLE 3

Comparison with REM Method and Combination with REM Method

EXAMPLE 3-1

(1) Induction of Anti-Influenza Virus Memory CTLs

The induction of anti-influenza virus memory CTLs was carried out in the same manner as in item (2) of Example 1-1 using the PBMCs which were separated and stored in the same manner as in item (1) of Example 1-1. During the The cytotoxic activity of CTLs on the fourteenth day after the initiation of induction which were prepared as described above was evaluated in the same manner as in item (3) of Example 1-1.

(2) Expansion of CTLs

CTLs prepared in item (1) of Example 3-1 were washed with 5HRPMI, and then made into a suspension having a concentration of $5 \times 10^4$ cells/ml. On the other hand, allogenic PBMCs not having HLA-A24 and HLA-A2.1 which were collected in the same manner as in item (1) of Example 1-1 were subjected to X-ray irradiation (3300R), and the cells were washed with the medium and then made into a suspension having a concentration of $5 \times 10^6$ cells/ml. These CTLs ($2.5 \times 10^4$ cells) and allogenic PBMCs ($1.25 \times 10^7$ cells) were suspended in 10 ml of 5HRPMI, and anti-CD3 antibody (manufactured by Janssen-Kyowa) was further added thereto so as to have a final concentration of 50 ng/ml. The mixture was placed into a flask of 12.5 $cm^2$ (manufactured by Falcon), and the cells were cultured in a wet-type $CO_2$ incubator at 37° C. for 14 days. During the culture, a group with addition of the fucoidan derived from *Kjellmaniella crassifolia* as a sample so as to have a final concentration of 10 μg/ml and a group with no addition of the sample were used. Stimulation by a peptide was not added at all during this culture. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 to each flask were carried out every 2 to 3 days. On this occasion, the fucoidan derived from *Kjellmaniella crassifolia* prepared in Preparation Example 1 was added to the medium for the group with addition of the sample so as to have a final concentration of 10 μg/ml. On the fourteenth day after the initiation of the expansion, the specific cytotoxic activity of CTLs was determined in the same manner as in item (3) of Example 1-1. The determination results are shown in Table 16.

On the other hand, the expansion according to the REM method was carried out as follows. Allogenic PBMCs not having HLA-A24 and HLA-A2.1 were subjected to X-ray irradiation (3300R), and the cells were washed with the medium and then made into a suspension having a concentration of $5 \times 10^6$ cells/ml. In addition, Epstein-Barr Virus-infected human B-cell line (EBV-B cells) was subjected to X-ray irradiation (3300R), and the cells were washed with the medium and then made into a suspension having a concentration of $1 \times 10^6$ cells/ml. The CTLs ($2.5 \times 10^4$ cells) prepared in item (1) of Example 3-1 and the allogenic PBMCs ($1.25 \times 10^7$ cells), and the EBV-B cells ($2.5 \times 10^6$ cells) were suspended in 10 ml of 5HRMPI, and anti-CD3 antibody (manufactured by Janssen-Kyowa) was further added so as to have a final concentration of 50 ng/ml. The mixture was placed into a flask of 12.5 cm$^2$ (manufactured by Falcon), and the cells were cultured in a wet-type $CO_2$ incubator at 37° C. for 14 days. During the culture, a group with addition of the fucoidan derived from *Kjellmaniella crassifolia* prepared in Preparation Example 1 as a sample so as to have a final concentration of 10 μg/ml and a group with no addition of the sample were used. The cells were prepared in the same manner as described above but not the EBV-B cells using the same flask, and the cells were also similarly cultured as described above. Stimulation by a peptide was not added at all during this culture. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 to each flask were carried out every 2 to 3 days. On this occasion, the fucoidan derived from *Kjellmaniella crassifolia* prepared in Preparation Example 1 was added to the medium for the group with addition of the sample so as to have a final concentration of 10 μg/ml. On the fourteenth day after the initiation of the expansion, the specific cytotoxic activity of CTLs was determined in the same manner as in item (3) of Example 1-1. The determination results are shown in Table 17.

TABLE 16

| | Addition of Sample | | | | | Cytotoxic Activity (%) E/T Ratio | | |
|---|---|---|---|---|---|---|---|---|
| Sample | During CTL Induction | During Expansion | Addition of EBV-B Cells | Expansion Ratio | Peptide Addition | 3 | 10 | 30 |
| Control | − | − | − | × 494 | − | 1.2 | 2.0 | 8.4 |
| | − | − | − | × 494 | + | 14.2 | 38.8 | 70.3 |
| Fucoidan Derived from *Kjellmaniella crassifolia* | − | + | − | × 694 | − | 2.2 | 5.8 | 7.8 |
| | − | + | − | × 694 | + | 26.4 | 62.3 | 83.8 |
| | + | − | − | × 488 | − | 3.2 | 7.2 | 18.5 |
| | + | − | − | × 488 | + | 44.7 | 84.2 | 102.6 |
| | + | + | − | × 513 | − | 3.2 | 5.4 | 7.6 |
| | + | + | − | × 513 | + | 47.4 | 87.0 | 108.3 |

TABLE 17

| | Addition of Sample | | | | | Cytotoxic Activity (%) E/T Ratio | | |
|---|---|---|---|---|---|---|---|---|
| Sample | During CTL Induction | During Expansion | Addition of EBV-B Cells | Expansion Ratio | Peptide Addition | 3 | 10 | 30 |
| Control | − | − | − | × 494 | − | 1.2 | 2.0 | 8.4 |
| | − | − | − | × 494 | + | 14.7 | 38.8 | 70.3 |
| REM Method | − | − | + | × 713 | − | 0 | 0 | 4.8 |
| | − | − | + | × 713 | + | 27.5 | 68.4 | 94.9 |
| REM Method + Fucoidan Derived from *Kjellmaniella crassifolia* | − | + | + | × 656 | − | 0.8 | 0.8 | 0 |
| | − | + | + | × 656 | + | 35.2 | 74.1 | 102.8 |
| | + | − | + | × 662 | − | 1.1 | 1.8 | 6.2 |
| | + | − | + | × 662 | + | 72.7 | 95.3 | 92.8 |
| | + | + | + | × 638 | − | 0 | 1.5 | 4.8 |
| | + | + | + | × 638 | + | 65.0 | 88.5 | 98.6 |

As a result, the CTLs which were induced without the addition of the fucoidan derived from *Kjellmaniella crassifolia* (with no addition of CTL inducer) maintained high cytotoxic activity when the expansion was carried out according to the REM method. However, the cytotoxic activity was drastically lowered when the expansion was carried out according to the REM method without using the EBV-B cells.

On the other hand, if the fucoidan derived from *Kjellmaniella crassifolia* was added in both stages or one of the stage during the CTL induction and the stage during the expansion, the cytotoxic activity of CTLs could be maintained at a sufficiently high level after expansion for 14 days even when the EBV-B cells were not added. Furthermore, the antigen-specific cytotoxic activity of CTLs after the expansion according to the present invention was higher as compared to that of the cells obtained according to the REM method.

In addition, when the expansion was carried out according to the REM method, the cytotoxic activity could be maintained at a high level by expanding the CTL cells which had been induced in the prior art simply by the REM method if the fucoidan derived from *Kjellmaniella crassifolia*, one of the compounds having effects for maintaining CTL activity according to the method of the present invention, was added at the stage of CTL induction prior to the expansion.

In other words, in the method for expansion in which the compound having the effects for maintaining CTL activity was added, the EBV-B cells which are essential in the REM method would not be required, so that the risks involved in the use of the EBV-B cells can be avoided. Furthermore, there can be maintained the activity of CTLs higher than that obtained by the REM method. From these findings, the method for expanding CTL cells of the present invention is a method which is safer and more excellent than the REM method.

Furthermore, when the compound used in the present invention is introduced in the REM method, CTLs having an even higher activity can be expanded. In other words, the compound used in the present invention can be applied to all sorts of methods for expanding CTLs. Therefore, it was clarified that specific, high cytotoxic activity can be maintained for a long period of time by using the compound used in the present invention in various methods for expanding CTLs.

EXAMPLE 3-2

(1) Induction of Anti-Influenza Virus Memory CTLs

The induction of anti-influenza virus memory CTLs was carried out in the same manner as in item (2) of Example 1-1 using the PBMCs which were separated and stored in the same manner as in item (1) of Example 1-1. During the induction, hyaluronic acid was added as a sample to a medium so as to have a final concentration of 10 μg/ml. Further, the group with no addition of sample was used.

The cytotoxic activity of CTLs on the fourteenth day after the initiation of induction which were prepared as described above was evaluated in the same manner as in item (3) of Example 1-1. As an antigenic peptide, FluMPA2.1 was used.

(2) Expansion of CTLs

CTLs prepared in item (1) of Example 3-2 were expanded in the same manner as in item (2) of Example 3-1. During the expansion, a group with addition of hyaluronic acid as a sample so as to have a final concentration of 10 μg/ml and a group with no addition of the sample were used. Stimulation by a peptide was not added at all during this culture. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 to each flask were carried out every 2 to 3 days. On this occasion, hyaluronic acid was added to the medium for the group with addition of the sample so as to have a final concentration of 10 μg/ml. On the fourteenth day after the initiation of the expansion, the specific cytotoxic activity of CTLs was determined in the same manner as in item (3) of Example 1-1. The determination results are shown in Table 18.

TABLE 18

| Sample | Addition of Sample | | | Expansion Ratio | Peptide Addition | Cytotoxic Activity (%) E/T Ratio 10 |
| | During CTL Induction | During Expansion | Addition of EBV-B Cells | | | |
|---|---|---|---|---|---|---|
| Control | − | − | − | × 392 | − | 6.2 |
|  | − | − | − | × 392 | + | 10.6 |
| Hyaluronic Acid | + | + | − | × 335 | − | 2.3 |
|  | + | + | − | × 335 | + | 60.0 |
| REM Method | − | − | + | × 427 | − | 11.5 |
|  | − | − | + | × 427 | + | 52.8 |
| REM Method + Hyaluronic Acid | + | + | + | × 587 | − | 8.1 |
|  | + | + | + | × 587 | + | 95.5 |

As a result, the CTLs which were induced without the addition of hyaluronic acid (with no addition of an agent for maintaining CTL activity) maintained high cytotoxic activity -when the expansion was carried out according to the REM method. However, the cytotoxic activity was drastically lowered when the expansion was carried out according to the REM method without using the EBV-B cells.

On the other hand, if hyaluronic acid was added in both of the stage during the CITL induction and the stage during the expansion, the cytotoxic activity of CTLs could be maintained at a sufficiently high level after expansion for 14 days even when the EBV-B cells were not added. Furthermore, the antigen-specific cytotoxic activity of CTLs after the expansion according to the present invention was higher as compared to that of the cells obtained according to the REM method.

In addition, when the expansion was carried out according to the REM method, the cytotoxic activity could be maintained at a high level by expanding the CTL cells which had been induced in the prior art simply by the REM method if hyaluronic acid, one of the compounds having effects for maintaining CTL activity according to the method of the present invention, was added at the stage of CTL induction prior to the expansion.

In other words, in the method for expanding CTL according to the present invention, the EBV-B cells which are essential in the REM method would not be required, so that the risks involved in the use of the EBV-B cells can be avoided. Furthermore, there can be maintained the activity of CTLs higher than that obtained by the REM method. From these findings, the method for expanding CTL cells of the present invention is a safer and more excellent method than the REM method.

Furthermore, when hyaluronic acid is introduced in the REM method, CTLs can have an even higher activity, and hyaluronic acid can be applied to all sorts of methods for expanding CTLs. Therefore, the expansion of CTLS can be carried out with maintaining specific, high cytotoxic activity for a long period of time by adding the compound used in the present invention in various methods for expanding CTLs.

EXAMPLE 4

Expansion of CTLs Having Specific Cytotoxic Activity Using Hyaluronic Acid

EXAMPLE 4-1

(1) Induction of Anti-Influenza Virus Memory CTLs

The induction of anti-influenza virus memory CTLs was carried out in the same manner as in item (2) of Example 1-1 using the PBMCs which were separated and stored in the same manner as in item (1) of Example 1-1. During the induction, hyaluronic acid (manufactured by Calbiochem) was added to a medium so as to have a final concentration of 10 μg/ml. Further, the group with no addition of hyaluronic acid was used. As an antigenic peptide, FluMPA2.1 was used.

The cytotoxic activity of CTLs on the fourteenth day after the initiation of induction which were prepared as described above was evaluated in the same manner as in item (3) of Example 1-1. As a result, the specific cytotoxic activity was induced immediately after the induction, but there was no difference in the cytotoxic activity by the presence or absence of the addition of the sample during the induction.

(2) Expansion of CTLs

CTLs prepared in item (1) of Example 4-1 were expanded in the same manner as in item (2) of Example 2-1. During the expansion, there were used a group with addition of the hyaluronic acid, which was added during the CTL induction in item (1) of Example 4-1 so as to have a final concentration of 10 μg/ml and a group with no addition of hyaluronic acid at all from the stage of the induction. Stimulation by a peptide was not added at all during this culture. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 Uml IL-2 and 10 μg/ml hyaluronic acid to each flask were carried out every 2 to 3 days. However, in the group with no addition of hyaluronic acid, the sample was not added even during medium exchange. On the fourteenth day after the initiation of the expansion, the specific cytotoxic activity of CT s was determined in the same manner as in item (3) of Example 1-1. The determination results are shown in Table 19.

TABLE 19

| | Addition of Sample | | | | Cytotoxic Activity (%) E/T Ratio | | | |
|---|---|---|---|---|---|---|---|---|
| Sample | During CTL Induction | During Expansion | Expansion Ratio | Peptide Addition | 1 | 3 | 10 | 30 |
| Control | − | − | × 547 | − | 7.3 | 8.4 | 9.1 | 12.7 |
| | − | − | × 547 | + | 8.1 | 11.2 | 21.5 | 45.9 |
| Hyaluronic Acid | + | + | × 493 | − | 7.3 | 8.6 | 13.1 | 17.0 |
| | + | + | × 493 | + | 31.1 | 49.8 | 90.8 | 105.6 |

As a result, in the group with addition of hyaluronic acid during the CTL induction and during the expansion, the CTLs had specific, high cytotoxic activity even after the expansion for 14 days. On the other hand, in the group with no addition of the sample in both of the stage during the CTL induction and the stage during the expansion, its activity was clearly lowered. In other words, it was clarified from the above that the expansion of CTLs could be carried out with maintaining a specific, high cytotoxic activity by adding hyaluronic acid at the stage during the CTL induction and at the stage during the expansion.

EXAMPLE 4-2

(1) Induction of Anti-Influenza Virus Memory CTLs

The induction of anti-influenza virus memory CTLs was carried out in the same manner as in item (2) of Example 1-1 using the PBMCs which were separated and stored in the same manner as in item (1) of Example 1-1. During the induction, hyaluronic acid was added to a medium so as to have a final concentration of 10 μg/ml. Further, the group with no addition of sample was used. As an antigenic peptide, FluMPA2.1 was used.

The cytotoxic activity of CTLs on the fourteenth day after the initiation of induction which were prepared as described above was evaluated in the same manner as in item (3) of Example 1-1. As a result, the specific cytotoxic activity was induced immediately after the induction, but there was no difference in the cytotoxic activity by the presence or absence of the addition of the sample during the induction.

(2) Expansion of CTLs

CTLs prepared in item (1) of Example 4-2 were expanded in the same manner as in item (2) of Example 2-1. During the expansion, the hyaluronic acid, which was added during the CTL induction in item (1) of Example 4-2, was not added at all. Stimulation by a peptide was not added at all during this culture. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 to each flask were carried out every 2 to 3 days. On the fourteenth day after the initiation of the expansion, the specific cytotoxic activity of CTLs was determined in the same manner as in item (3) of Example 1-1. The determination results are shown in Table 20.

TABLE 20

| | Addition of Sample | | | | Cytotoxic Activity (%) E/T Ratio | | | |
|---|---|---|---|---|---|---|---|---|
| Sample | During CTL Induction | During Expansion | Expansion Ratio | Peptide Addition | 1 | 3 | 10 | 30 |
| Control | – | – | × 480 | – | 0 | 0 | 0.4 | 6.8 |
| | – | – | × 480 | + | 4 | 11.2 | 29.3 | 59.7 |
| Hyaluronic Acid | + | + | × 423 | – | 0 | 0 | 1.9 | 14.3 |
| | + | + | × 423 | + | 7.2 | 23.3 | 59.6 | 85.1 |
| | + | – | × 393 | – | 3.0 | 1.4 | 4.7 | 9.3 |
| | + | – | × 393 | + | 9.9 | 22.1 | 47.7 | 78.0 |

As a result, in the group with addition of hyaluronic acid only during the CTL induction, the CTLs had specific, high cytotoxic activity even after the expansion for 14 days even when hyaluronic acid was not added during the expansion. On the other hand, in the group with no addition of the sample in both of the stage during the CTL induction and the stage during the expansion, its activity was clearly lowered. In other words, it was clarified from the above that the expansion of CTLs could be carried out with maintaining a specific, high cytotoxic activity by adding hyaluronic acid only at the stage during the CTL induction.

EXAMPLE 5

Expansion of CTLs Having Tumor-Associated Antigen Specific Cytotoxic Activity

EXAMPLE 5-1

(1) Induction of Anti-Tumor-Associated Antigen(MAGE3)-Specific CTLs

The induction of anti-tumor-associated antigen(MAGE3)-specific CTLs was performed using the PBMCs which were separated and stored according to the method described in item (1) of Example 1-1. The induction of the anti-tumor-associated antigen (MAGE3)-specific CTLs was performed by partially modifying the method of Plebanski et al. (*Eur. J. Immunol.* (1994) 25, 1783-1787). Concretely, PBMCs prepared in item (1) of Example 1-1 were suspended in RPMI 1640 medium (manufactured by Bio Whittaker) containing 5% human AB-type serum, 0.1 mM nonessential amino acids, 1 mM sodium pyruvate, 2 mM L-glutamine (hereinabove being all manufactured by Bio Whittaker), 10 mM HEPES (manufactured by nakalai tesque), 1% streptomycin-penicillin (manufactured by Gibco BRL) (hereinafter simply referred to as "5HRPMI") so as to have a concentration of 2 to $4 \times 10^7$ cells/ml, and then the suspension was divided into halves. A half of the suspension was stored on ice as responder cells, and the other half was used as antigen-presenting cells. An equivolume of 5HRPMI containing as an antigen peptide a 80 µg/ml epitope peptide derived from melanoma antigen MAGE3 (HLA A2.1-binding peptide derived from melanoma antigen MAGE3 of SEQ ID NO: 3 of Sequence Listing, FLWGPRALV) and 6 µg/ml β2 microglobulin (manufactured by Scripts) was added. The cells were incubated in a 5% $CO_2$ wet-type incubator at 37° C. for 2 hours. Thereafter, the cells were washed with 5HRPMI, and thereafter mixed with the responder cells stored on ice and then made into a suspension so as to have a concentration of $2 \times 10^6$ cells/ml. IL-7 and KLH were added to the suspension so as to have final concentrations of 25 ng/ml and 5 µg/ml, respectively. The resulting suspension was poured into 24-well culture plate (manufactured by Falcon) in an amount of 2 ml per each well. On this occasion, L. M. W. heparin (manufactured by Seikagaku Corporation) or hyaluronic acid (manufactured by Calbiochem) was added so as to have a final concentration of 10 µg/ml. As the control, a group with no addition of the sample was used. The cells in the plate were cultured at 37° C. in 5% $CO_2$.

A half of the culture supernatant was removed on the fourth day after the initiation of culture, and thereafter 1 ml of 5 HRPMI containing 60 U/ml IL-2 and the 10 µg/ml L. M. W. heparin or hyaluronic acid (the control containing only IL-2) was added to each well.

On the seventh day the antigen-presenting cells were prepared in the same manner as above, and thereafter the cells were subjected to X-ray irradiation (5500R) and then made into a suspension having a concentration of $4 \times 10^6$ cells/ml. The responder cells which were cultured for one week were suspended in 5HRPMI so as to have a concentration of $2 \times 10^6$ cells/ml, and mixed in an equivolume with the prepared antigen-presenting cells. The resulting suspension was added into a 24-well cell culture plate in an amount of 1 ml per each well, IL-7 was additionally added so as to have a final concentration of 25 ng/ml to re-stimulate the cells. On this occasion, L. M. W. heparin or hyaluronic acid was added so as to have a final concentration of 10 µg/ml (the control being no addition). On the first day after the re-stimulation, 1 ml of 5HRPMI containing 60 U/ml IL-2 and the 10 µg/ml L. M. W. heparin or hyaluronic acid (the control containing only IL-2) was added to each well. Also, on the third day, a half of the culture supernatant was removed, and thereafter 1 ml of the medium having the same content as that before removal was added per each well. The same re-stimulation procedures were carried out once a week for a total of four times, thereby inducing CTLS.

(2) Determination for Cytotoxic Activity of CTLs

The cytotoxic activity of CTLs on the thirty-fifth day after the initiation of induction prepared in item (1) of Example 5-1 was evaluated in the same manner as in item (3) of Example 1-1. In the evaluation, as target cells, HLA-A2.1-having EBV transformed B-cells (221A2.1), which were cultured overnight together with an epitope peptide or in the absence of the epitope peptide (name of cells: 221A2.1) were used.

As a result, the specific cytotoxic activity was induced immediately after the induction, but there was almost no difference in the cytotoxic activity by the presence or absence of the addition of L. M. W. heparin and hyaluronic acid during the induction.

(3) Expansion of CTLs

CTLs prepared in item (1) of Example 5-1 were expanded in the same manner as in item (2) of Example 2-1. During the expansion, a group with addition of L. M. W. heparin or hyaluronic acid, which was added during the CTL induction in item (1) of Example 5-1 so as to have a concentration of 10 μg/ml and a group with no addition of the sample at all from the stage during the induction were used. Stimulation by a peptide was not added at all during this culture. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 and 10 μg/ml L. M. W. heparin or hyaluronic acid to each flask were carried out every 2 to 3 days. However, in the group with no addition of the sample, the sample was not added even during medium exchange. On the fourteenth day after the initiation of the expansion, the specific cytotoxic activity of CTLs was determined in the same manner as in item (3) of Example 1-1. The determination results are shown in Table 21.

TABLE 21

| Sample | Addition of Sample During CTL Induction | During Expansion | Expansion Ratio | Peptide Addition | Cytotoxic Activity (%) | |
|---|---|---|---|---|---|---|
| | | | | | E/T Ratio | |
| | | | | | 2 | 6 |
| Control | − | − | × 237 | − | 0 | 0 |
| | − | − | × 237 | + | 29.8 | 56 |
| | | | | | E/T Ratio | |
| | | | | | 3 | 9 |
| L. M. W. | + | + | × 433 | − | 2.6 | 3.7 |
| Heparin | + | + | × 433 | + | 65.3 | 104.8 |
| | | | | | E/T Ratio | |
| | | | | | 2 | 6 |
| Hyaluronic | + | + | × 217 | − | 3.6 | 0 |
| Acid | + | + | × 217 | + | 50.3 | 67.7 |

As a result, in the group with addition of L. M. W. heparin or hyaluronic acid at the stage during the CTL induction and at the stage during the expansion, the CTLs had specific, high cytotoxic activity even after the expansion for 14 days. On the other hand, in the group with no addition of these samples in both of the stage during the CTL induction and the stage during the expansion, its activity was clearly lowered. In other words, it was clarified from the above that the expansion of CTLs could be carried out with maintaining also in the stage during the expansion of anti-tumor-associated antigen (MAGE3)-specific CTLs a specific, high cytotoxic activity for a long period of time by adding L. M. W. heparin or hyaluronic acid in the stage during the CTL induction and the stage during the expansion.

EXAMPLE 5-2

(1) Induction of Anti-Tumor-Associated Antigen(MART1)-Specific CTLs

The induction of anti-tumor-associated antigen(MART1)-specific CTLs was carried out in the same manner as in item (1) of Example 5-1 using PBMCs which were separated and stored according to the method described in item (1) of Example 1-1. As an antigen peptide, an epitope peptide derived from melanoma antigen MART1 (HLA A2.1-binding peptide derived from melanoma antigen MART1 of SEQ ID NO: 4 of Sequence Listing, AAGIGILTV). During the CTL induction, the fucoidan derived from *Kjellmaniella crassifolia* or hyaluronic acid (manufactured by Calbiochem) was added to the medium so as to have a final concentration of 10 μg/ml. Also, as the control, a group with no addition of the sample was used.

The cytotoxic activity of CTLs immediately after the induction which were thus prepared as described above was evaluated in the same manner as in item (3) of Example 1-1. In the evaluation, as target cells, there were used HLA-A2.1-having EBV transformed B-cells which were cultured in the absence of the epitope peptide (name of cells: 221A2.1); a cancer cell line-having HIA-A2.1 which was cultured for two nights in the presence of 100 U/ml IFN-γ (name of cells: 624mel; MART1 expressed cells having HLA-A2.1); or a cancer cell line not having HLA-A2.1 (name of cells: 888mel; MART1 expressed cells not having HLA-A2.1).

As a result, the specific cytotoxic activity was induced immediately after the induction, but there was almost no difference in the cytotoxic activity by the presence or absence of the addition of the sample during the induction.

(2) Expansion of CTLs

CTLs prepared in item (1) of Example 5-2 were expanded in the same manner as in item (2) of Example 2-1. During the expansion, there were used a group with addition of the fucoidan derived from *Kjellmaniella crassifolia* or the hyaluronic acid, which was added during the CTL induction in item (1) of Example 5-2 so as to have a concentration of 10 μg/ml and a group with no addition of the sample at all from the stage of the induction. Stimulation by a peptide was not added at all during this culture. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 and 10 μg/ml the fucoidan derived from *Kjellmaniella crassifolia* or hyaluronic acid to each flask were carried out every 2 to 3 days. However, in the group with no addition of the sample, the sample was not added even during medium exchange. On the fourteenth day after the initiation of the expansion, the specific cytotoxic activity of CTLs was determined in the same manner as in item (3) of Example 1-1. The determination results are shown in Table 22.

TABLE 22

| Sample | During CTL Induction | During Expansion | Expansion Ratio | Peptide Addition | Target Cells | Cytotoxic Activity (%) E/T Ratio | | |
|---|---|---|---|---|---|---|---|---|
| | | | | | | 2 | 7 | 20 |
| Control | − | − | × 287 | − | 221A2.1 | 0 | 3.8 | 4.1 |
| | − | − | × 287 | + | 221A2.1 | 8.1 | 27.5 | 43.5 |
| | − | − | × 287 | − | 888mel | 32.5 | 44.8 | 43.7 |
| | − | − | × 287 | − | 624mel | 27.4 | 55.8 | 81.6 |
| | | | | | | 2 | 6 | 17 |
| Fucoidan Derived from *Kjellmaniella crassifolia* | + | + | × 240 | − | 221A2.1 | 0 | 0 | 0 |
| | + | + | × 240 | + | 221A2.1 | 28.8 | 63.2 | 84.0 |
| | + | + | × 240 | − | 888mel | 8.2 | 22.4 | 19.2 |
| | + | + | × 240 | − | 624mel | 40.7 | 78.5 | 92.2 |
| | | | | | | 2 | 6 | 17 |
| Hyaluronic Acid | + | + | × 217 | − | 221A2.1 | 0 | 0 | 0 |
| | + | + | × 217 | + | 221A2.1 | 9.1 | 52.8 | 74.4 |
| | + | + | × 217 | − | 888mel | 0 | 0 | 0 |
| | + | + | × 217 | − | 624mel | 29.6 | 73.8 | 90.6 |

As a result, in the group with addition of the fucoidan derived from *Kjellmaniella crassifolia* or hyaluronic acid during the CTL induction and during the expansion, the CTLs had specific, high cytotoxic activity even after the expansion for 14 days. On the other hand, in the group with no addition of these samples in both of the stage during the CTL induction and the stage during the expansion, its activity was clearly lowered. In addition, with regard to the specific cytotoxic activity for a tumor cell line, in the group with addition of the fucoidan derived from *Kjellmaniella crassifolia* or hyaluronic acid at the stage during the CTL induction and at the stage during the expansion, CTLs had specific, high cytotoxic activity even after the expansion was carried out for 14 days. In other words, the expansion of CTLs could be also carried out with maintaining a specific, high cytotoxic activity during the expansion of anti-tumor-associated antigen(MART1)-specific CTLs by adding the fucoidan derived from *Kjellmaniella crassifolia* or hyaluronic acid at the stage during the CTL induction and at the stage during the expansion.

EXAMPLE 6

Selection of Cells by Antibody-Binding Magnetic Beads

EXAMPLE 6-1

(1) Induction of Anti-Influenza Virus Memory CTLs

The induction of anti-influenza virus memory CTLs was carried out in the same manner as in item (2) of Example 1-1 using the PBMCs which were separated and stored according to the method described in item (1) of Example 1-1. During the induction, the fucoidan derived from *Kjellmaniella crassifolia* was added to a medium so as to have a final concentration of 10 µg/ml. Further, the group with no addition of the fucoidan derived from Kjellmaniella crassifolia was used.

The cytotoxic activity of CTLs on the fourteenth day after the initiation of induction which were prepared as described above was evaluated in the same manner as in item (3) of Example 1-1. As a result, the specific cytotoxic activity was induced immediately after the induction, but there was almost no difference in the cytotoxic activity by the presence or absence of the addition of the sample during the induction.

(2) Expansion of CTLs

CTLs prepared in item (1) of Example 6-1 were expanded in the same manner as in item (2) of Example 3-1. During the expansion, there were used the group with the addition of the fucoidan derived from *Kjellmaniella crassifolia* as a sample so as to have a final concentration of 10 µg/ml and the group with addition of no sample. Stimulation by a peptide was not added at all during this culture. On the first day of the initiation of the culture, IL-2 was added so as to have a final concentration of 120 U/ml. Further, on the fourth day and on after the initiation of the culture, procedures of removing a half of the culture supernatant, and thereafter adding 5 ml of 5HRPMI containing 60 U/ml IL-2 to each flask were carried out every 2 to 3 days. On this occasion, the fucoidan derived from *Kjellmaniella crassifolia* was added to the medium for the group with addition of the sample so as to have a final concentration of 10 µg/ml. On the fourteenth day after the initiation of the expansion, the specific cytotoxic activity of CTLs was determined in the same manner as in item (3) of Example 1-1.

(3) Selection of Cells by Antibody-Binding Magnetic Beads

The CTLs after the expansion prepared in item (2) of Example 6-1 were washed with ice-cooled 2% FBS/PBS, and the resulting suspension was prepared so as to have a concentration of 1×10⁷ cells/ml with the same buffer. Dynabeads M-450 CD4 (anti-CD4-antibody-binding magnetic beads, manufactured by Dynal), which were previously washed with ice-cooled 2% FBS/PBS, were added to these cell suspensions in an amount of 150 μl per 1×10⁷ cells, respectively. The beads-containing cell suspension was incubated for 30 minutes at 4° C. with gently shaking. Ice-cooled 2% FBS/PBS was added to a tube containing the incubated cell suspension, and beads and beads-binding cells were removed by using a magnetic stand for Dynabeads (manufactured by Dynal). The content of CD8+cells for the anti-CD4-antibody-binding beads-nonbinding cell population and the cell population before the selection was confirmed using a flow cytometer. The results are shown in Table 23. Furthermore, the cytotoxic activity of CTLs was compared in the same manner as in item (3) of Example 1-1. The results are shown in Table 24.

TABLE 23

| Sample | Addition of Sample | | Addition of EBV-B Cells | Content of CD8+ Cells (%) | |
|---|---|---|---|---|---|
| | During CTL Induction | During Expansion | | Before Selection | After Selection |
| Control | − | − | − | 18.1 | 88.0 |
| Fucoidan Derived from *Kjellmaniella crassifolia* | + | + | − | 32.5 | 97.2 |
| REM Method + Fucoidan Derived from *Kjellmaniella crassifolia* | + | + | + | 55.8 | 97.3 |

TABLE 24

| Sample | Addition of Sample | | | | Cytotoxic Activity (%) (E/T Ratio = 30) | |
|---|---|---|---|---|---|---|
| | During CTL Induction | During Expansion | EBV-B Cells | Peptide Addition | Before Selection | After Selection |
| Control | − | − | − | − | 10.4 | 9.4 |
| | − | − | − | + | 24.0 | 21.1 |
| Fucoidan Derived from *Kjellmaniella crassifolia* | + | + | − | − | 7.6 | 8.4 |
| | + | + | − | + | 41.8 | 75.3 |
| REM Method + Fucoidan Derived from *Kjellmaniella crassifolia* | + | + | + | − | 4.2 | 6.7 |
| | + | + | + | + | 87.8 | 88.2 |

As a result, in the groups with addition of the fucoidan derived from *Kjellmaniella crassifolia* during the CTL induction and during the expansion, their cytotoxic activities could be made even higher by selecting the cells with the antibody-binding beads. In addition, when the CTLs were cultured according to the REM method and the cells were selected with the antibody-binding beads, their cytotoxic activities did not change. In addition, when the expansion was carried out under the conditions of the REM method and the addition of the fucoidan derived from *Kjellmaniella crassifolia*, and then the cells were selected with the antibody-binding beads, their cytotoxic activities can be made even higher.

Deposited Biological Materials (1) Name and Addressee of Depository Authority the International Patent Organism Depositary, National Institute of Advanced Industrial Science and Technology Tsukuba Central 6, 1-1, Higashi 1-chome Tsukuba-shi, Ibaraki-ken, Japan (Zip code 305-8566)

(2) Deposited Microorganisms (i) *Alteromonas* sp. SN-1009

Original Date of Deposit: Feb. 13, 1996

Date of Request for Transfer to International Deposit: Nov. 15, 1996

Accession Number: FERM BP-5747

(ii) *Flavobacterium* sp. SA-0082

Original Date of Deposit: Mar. 29, 1995

Date of Request for Transfer to International Deposit: Feb. 15, 1996

Accession Number: FERM BP-5402

Sequence Free Text

SEQ ID NO: 1 is HLA A24-binding peptide which is designed based on nucleoprotein derived from influenza virus.

SEQ ID NO: 2 is HLA A2.1-binding peptide which is designed based on matrixprotein derived from influenza virus.

SEQ ID NO: 3 is the peptide which is designed based on HLA-A21-binding peptide derived from melanoma antigen MAGE3.

SEQ ID NO: 4 is the peptide which is designed based on HLA-A21-binding peptide derived from melanoma antigen MART1.

INDUSTRIAL APPLICABILITY

According to the present invention, there is provided a method for inducing, maintaining and expanding CTL having antigen-specific cytotoxic activity at a high level. This method is extremely useful in the field of cell remedy such as adoptive immunotherapy requiring a large amount of CTLs. In addition, since the CTL prepared by this method is prepared by a safe method, the CTL can be a cell medicament having very high safety.

The invention claimed is:

1. A method for inducing a cytotoxic T cell having an antigen-specific cytotoxic activity from a precursor cell capable of differentiating to a cytotoxic T cell, which comprises:
   incubating a precursor cell capable of differentiating to cytotoxic T cell with an antigen presenting cell in the presence of at least one compound selected from the group consisting of hyaluronic acid and salts thereof, wherein the content of said compound is from 0.001 to 1000 µg/ml.

2. A method for maintaining cytotoxic T cell having an antigen-specific cytotoxic activity, wherein the method comprises:

(1) incubating a precursor cell capable of differentiating to cytotoxic T cell with an antigen presenting cell in the presence of at least one compound selected from the group consisting of hyaluronic acid and salts thereof, wherein the content of said compound is from 0.001 to 1000 µg/ml to induce a cytotoxic T cell having an antigen-specific cytotoxic activity, and (2) continuously culturing the induced cytotoxic T cell obtained from step (1) in the presence of at least one compound selected from the group consisting of hyaluronic acid and salts thereof.

3. A method for expanding a cytotoxic T cell having an antigen-specific cytotoxic activity, which comprises:

(1) incubating a precursor cell capable of differentiating to cytotoxic T cell with an antigen presenting cell in the presence of at least one compound selected from the group consisting of hyaluronic acid and salts thereof, wherein the content of said compound is from 0.001 to 1000 μg/ml to induce a cytotoxic T cell having an antigen-specific cytotoxic activity, and (2) incubating the induced cytotoxic T cell obtained by step (1) in the presence of at least one compound selected from the group consisting of hyaluronic acid and salts thereof.

4. The method according to claim 3, wherein the cytotoxic T cell is incubated further in the presence of anti-CD3 antibody in said step.

5. The method according to claim 3 or 4, wherein the cytotoxic T cell is incubated together with a feeder cell in said step.

6. The method according to claim 5, wherein the feeder cell is a non-virus-infected cell.

7. A method for collecting a cytotoxic T cell, which comprises:

selecting a cell population rich in cytotoxic T cells having an antigen-specific cytotoxic activity from a culture containing the cytotoxic T cell obtained by the method of any one of claims 1, 2 and 3; and collecting said cell population.

* * * * *